United States Patent [19]

Godwin

[11] Patent Number: 5,801,041
[45] Date of Patent: Sep. 1, 1998

[54] GENE ASSOCIATED WITH SUPPRESSION OF TUMOR DEVELOPMENT

[75] Inventor: Andrew K. Godwin, Philadelphia, Pa.

[73] Assignee: Fox Chase Cancer Center, Philadelphia, Pa.

[21] Appl. No.: 399,986

[22] Filed: Mar. 6, 1995

[51] Int. Cl.[6] ............................................ C12N 1/20
[52] U.S. Cl. .................................................. 435/252.3
[58] Field of Search .......................... 536/24.3, 231, 536/23.5; 435/69.1, 240.1, 320.1, 252.3

[56] References Cited

PUBLICATIONS

Mukamura et al 1988 Nucleic Acids Res. 1612): 782.
Foulkes et al 1993 Int J Cancer 54: 220–225.
Schultz et al. 1995 Am J Hum Genet. 57(4Suppl) : A4.
Stenesh 1989. Dictionary of Biochemistry and Molecular Biology, 2nd Edition John Wiley & Sons, New York p. 164.
Coles et al., 1990, Lancet 336:761–763.
Cornelis et al., 1994, Cancer Research 54:4200–4206.
Bobyns et al., 1993, JAMA 270:2838–2842.
Futreal et al., 1994, Science 266:120–122.
Godwin et al., 1994, Am. J. Hum. Gen. 55:666–677.
Harris, 1993, Science 262:1980–1981.
Ledbetter et al., 1989, PNAS 86:5136–5140.
Ledbetter et al., 1990, Genomics 7:264–269.
Miki et al., 1994, Science 266:66–71.
Reiner et al., 1993, Nature 364:717–720.

*Primary Examiner*—Robert A. Wax
*Assistant Examiner*—Karen Cochrane Carlson
*Attorney, Agent, or Firm*—Dann, Dorfman, Herrell and Skillman

[57] ABSTRACT

This invention provides a novel gene, OVCA1, isolated from human chromosome 17p13.3. Disruption of the OVCA1 gene is associated with cellular proliferation and tumor development. The OVCA1 gene, along with its encoded protein and antibodies thereto, provides a biological marker for early diagnosis of metastatic disease. The gene also will be useful in gene replacement therapy for treating various forms of cancer.

3 Claims, 9 Drawing Sheets

```
                      MetArg  ArgGlnValMet AlaAlaLeuVal ValSerGlyAla    14
  1 CTGTCTTTTAG TACCACATGCGC AGGCAGGTGATG GCGGCGCTGGTC GTATCCGGGGCA     41
-18

15 AlaGluGlnGly GlyArgAspGly ProGlyArgGly ArgAlaProArg GlyArgValAla    34
 42 GCGGAGCAGGGC GGCCGAGACGGC CCTGGCAGAGGT CGGGCCCCTCGG GGCCGCGTGGCC   101

35 AsnGlnIlePro ProGluIleLeu LysAsnProGln LeuGlnAlaAla IleArgValLeu    54
102 AATCAGATCCCC CCTGAGATCCTG AAGAACCCTCAG CTGCAGGCAGCA ATCCGGGTCCTG   161

55 ProSerAsnTyr AsnPheGluIle ProLysThrIle TrpArgIleGln GlnAlaGlnAla    74
162 CCTTCCAACTAC AACTTTGAGATC CCCAAGACCATC TGGAGGATCCAA CAAGCCCAGGCC   221

75 LysLysValAla LeuGlnMetPro GluGlyLeuLeu LeuPheAlaCys ThrIleValAsp    94
222 AAGAAGGTGGCC TTGCAAATGCCG GAAGGCCTCCTC CTCTTTGCCTGT ACCATTGTGGAT   281

95 IleLeuGluArg PheThrGluAla GluValMetVal ThrTyrGlyAla              114
282 ATCTTGGAAAGG TTCACGGAGGCC GAAGTGATGGTG ACCTACGGGGCT                 341

115 CysCysValAsp AspPheThrAla ArgAlaLeuGly AlaAspPheLeu ValHisTyrGly   134
342 TGCTGTGTGGAT GACTTCACAGCG AGGGCCCTGGGA GCTGACTTCTTG GTGCACTACGGC   401

135 HisSerCysLeu IleProMetAsp ThrSerAlaGln AspPheArgVal LeuTyrValPhe   154
402 CACAGTTGCCTG ATTCCCATGGAC ACCTCGGCCCAA GACTTCCGGGTG CTGTACGTCTTT   461

155 ValAspIleArg IleAspThrThr HisLeuLeuAsp SerLeuArgLeu ThrPheProPro   174
462 GTGGACATCCGG ATAGACACTACA CACCTCCTGGAC TCTCTCCGCCTC ACCTTTCCCCCA   521
```

Fig. 2

| | | | | |
|---|---|---|---|---|
| 175 | AlaThrAlaLeu | AlaLeuValSer | ThrIleGlnPhe | ValSerThrLeu | GlnAlaAlaAla | 194 |
| 522 | GCCACTGCCCTT | GCCCTGGTCAGC | ACCATTCAGTTT | GTGTCGACCTTG | CAGGCAGCCGCC | 581 |
| 195 | GlnGluLeuLys | AlaGluTyrArg | ValSerValPro | GlnCysLysPro | LeuSerProGly | 214 |
| 582 | CAGGAGCTGAAA | GCCGAGTATCGT | GTGAGTGTCCCA | CAGTGCAAGCCC | CTGTCCCCTGGA | 641 |
| 215 | GluIleLeuGly | CysThrSerPro | ArgLeuSerArg | GluValGluAla | ValValTyrLeu | 234 |
| 642 | GAGATCCTGGGC | TGCACATCCCCC | CGACTGTCCAGA | GAGGTGGAGGCC | GTTGTGTATCTT | 701 |
| 235 | GlyAspGlyArg | PheHisLeuGlu | SerValMetIle | AlaAsnProAsn | ValProAlaTyr | 254 |
| 702 | GGAGATGGCCGC | TTCCATCTGGAG | TCTGTCATGATT | GCCAACCCCAAT | GTCCCCGCTTAC | 761 |
| 255 | ArgTyrAspPro | TyrSerLysVal | LeuSerArgGlu | HisTyrAspHis | GlnArgMetGln | 274 |
| 762 | CGGTATGACCCA | TATAGCAAAGTC | CTATCCAGAGAA | CACTATGACCAC | CAGCGCATGCAG | 821 |
| 275 | AlaAlaArgGln | GluAlaIleAla | ThrAlaArgSer | AlaLysSerTrp | GlyLeuIleLeu | 294 |
| 822 | GCTGCTCGCCAA | GAAGCCATAGCC | ACTGCCCGCTCA | GCTAAGTCCTGG | GGCCTTATTCTG | 881 |
| 295 | GlyThrLeuGly | ArgGlnGlySer | ProLysIleLeu | GluHisLeuGlu | SerArgLeuArg | 314 |
| 882 | GGCACTTTGGGG | CGCCAGGGCAGT | CCTAAGATCCTG | GAGCACCTGGAA | TCTCGACTCCGA | 941 |
| 315 | AlaLeuGlyLeu | SerPheValArg | LeuLeuLeuSer | GluIlePhePro | SerLysLeuSer | 334 |
| 942 | GCCTTGGGCCTT | TCCTTTGTGAGG | CTGCTGCTCTCT | GAGATCTTCCCC | AGCAAGCTTAGC | 1001 |
| 335 | LeuLeuProGlu | ValAspValTrp | ValGlnValAla | CysProArgLeu | SerIleAspTrp | 354 |
| 1002 | CTACTTCCCGAG | GTGGATGTGTGG | GTGCAGGTGGCA | TGTCCACGTCTC | TCCATTGACTGG | 1061 |
| 355 | GlyThrAlaPhe | ProLysProLeu | LeuThrProTyr | GluAlaAlaVal | AlaLeuArgAsp | 374 |
| 1062 | GGCACAGCCTTC | CCCAAGCCCCTG | CTGACACCCTAT | GAGGCGGCCGTG | GCTCTGAGGGAC | 1121 |
| 375 | IleSerTrpGln | GlnProTyrPro | MetAspPheTyr | AlaGlyArgSer | LeuGlyProTrp | 394 |
| 1122 | ATTTCCTGGCAG | CAGCCCTACCCG | ATGGACTTCTAC | GCTGGCAGATCC | TTGGGGCCCTGG | 1181 |

Fig. 2 (continued)

```
395   ThrValAsnHis GlyGlnAspArg ArgProHisAla ProGlyArgSer AlaArgGlyLys  414
1182  ACGGTGAACCAC GGGCAGGACCGT CGTCCCCACGCC CCGGGTCGGTCC GCGCGGGGAAG   1241

415   ValGlnGluGly SerAlaArgPro ProSerValVal ValCysGluAsp CysSerCysArg  434
1242  GTGCAGGAGGGG TCCGCGCGTCCC CCTTCGGTCGTG GTTTGCGAGGAC TGCAGCTGCAGG  1301

435   AspGluLysVal AlaProValAsp ProTrpThrArg SerArgAlaSer GlySerCysPro  454
1302  GACGAGAAGGTG GCGCCGGTGGAT CCCTGGACGCGC TCCCGGGCCTCA GGGTCCTGCCCT  1361

455   ProGluGluGln ProArgGlyTrp TrpPheSerGlu GlnGluAlaAsp ValPheSerAla  474
1362  CCGGAGGAGCAG CCTCGAGGCTGG TGGTTTTCAGAG CAGGAAGCCGAC GTTTTCTCCGCA  1421

475   LeuGluGluPro AlaValCysArg GlyLeuGluGlu SerLeuGlyMet ValAlaGlnAla  494
1422  TTGGAAGAGCCC GCCGTCTGCAGG GGCCTGGAGGAA TCACTGGGGATG GTGGCACAGGCA  1481

495   LeuAsnArgLeu GlyProPheAsp GlyLeuLeuGly PheSerGlnGly AlaAlaLeuThr  514
1482  CTGAACAGGCTG GGGCCTTTTGAC GGCCTTCTTGGT TTCAGCCAAGGG GCTGCGGCTAACA 1541

515   IleProCysVal TyrProGlyPro GlyArgArgSer ProLeuProLeu ThrThrGlyLeu  534
1542  ATCCCCTGTGTG TACCCTGGGCCA GGCAGGCGATCC CCGCTTCCCCTT ACCACGGGTTTA  1601

535   SerSerTrpCys LeuValSerVal ProGlyAlaLeu GlySerArgAsn ProSerSerLys  554
1602  TCCTCTTGGTGT CTAGTTTCTGTC CCCGGGGCATTG GGTTCAAGGAAT CCATCCTCCAAA  1661

555   GlyProCysHis CysLeuArgSer MetPheLeuGly ThrLeuThrLys SerSerProLeu  574
1662  GGCCCTTGTCAT TGCCTTCGCTCC ATGTTTTTGGGG ACACTGACAAAG TCATCCCCTCTC  1721
```

Fig. 2 (continued)

```
575   ArgArgValCys AsnTrpProAla ProSerProSer ProThrLeuVal   594
1722  AGGAGAGTGTGC AACTGGCCAGCC CCATCACCCTCA CCCACTCTGGTG   1781

595   AlaThrSerPhe GlnGlnLeuHis ProSerValArg ProThrThrSer   614
1782  GCCACTTCATTC CAGCAGCTGCAC CCCAGCGTCAGG CCTACCTCAAGT   1841

615   LeuGlnSerGlu ArgSerArgAsn ValSerAlaPro ThrSerSerSer   634
1842  TTGCAGAGTGAA AGATCAAGAAAT GTCTCTGCTCCT ACATCCAGCTCC   1901

635   SerArgGlySer LeuArgHisPro CysProProArg ThrLeuHisSer LeuLeu   654
1902  TCTAGGGGCAGC CTCCGTCATCCA TGCCCCTCCCAGG ACCCTCCACTCA CTGCTGTGAGTG   1961

1962  AATTATAAGGGC ACAACTATCAAT TCTTGAGACCCA CGCCCTCACCAGA   2021
                                                          CCTGCCCTGTAC

2022  TGAAGAAAAGGG GAGCACAAGGCC TTAATGGACATT GACTTGTGAAAA   2081
                                                          CGCAAACATGAA

2082  TATGGTTGGAGA GCCCTGGATTAG GAGGGTGACATG GGGAAGGCAGAG   2141
                                                          GCTGGCACGATG

2142  GTGACTGCCACA TAATAAAGTGGT GATTTGGATTTT GNAAAAA        2184
```

```
   1  GNCCATTACC AATCGCGAAA CCAGCGACCC CTGCGGGTCC TGTGCCTGGC
  51  GGGCTTCCGG CAGAGCGAGC GGGGCTTCCG TGAGAAGACC GGGGCGCTGA
 101  GGAAGGCGCT GCGGGTCGCG CCGAGCTCGT GTGCCTCAGC GCCCGCACCC
 151  GGTCCCCGAC CCCCGGGCC CCGAGGGCGC CAGATCAGAC TTCGGGTCCT
 201  GCCCTCCGGA GGAGCAGCCT CGAGGCTGGT GGTTTTCAGA GCAGGAGGCC
 251  GACGTTTTCT CCGCATTGGA AGAGCCCGCC GTCTGCAGGG GCCTGGAGGA
 301  ATCACTGGGG ATGGTGGCAC AGGCACTGAA CAGGCTGGGG CCTTTTGACG
 351  GCCTTCTTGG TTTCAGCCAA GGGGCTGCGC TAACAATCCC TTGTGTGTAC
 401  CCTGGGCCAG GCAGGCGATC CCGCTTCCC CTTACCACGG GTTTATCCTC
 451  TTGGTGTCTA GTTTCTGTCC CCGGGGCATT GGGTTCAAGG AATCCATCCT
 501  CCAAAGGCCC TTGTCATTGC CTTCGCTCCA TGTTTTTGGG GACACTGACA
 551  AAGTCATCCC CTCTCAGGAG AGTGTGCAAC TGGCCAGCCA ATTTCCCGGA
 601  GCCATCACCC TCACCCACTC TGGTGGCCAC TTCATTCCAG CAGCTGCACC
 651  CCAGCGTCAG GCCTACCTCA AGTTCTTGGA CCAGTTTGCA GAGTGAAAGA
 701  TCAAGAAATG TCTCTGCTCC TACATCCAGC TCCTCTAGGG GCAGCCTCCG
 751  TCATCCATGC CCTCCCAGGA CCCTCCACTC ACTGCTGTGA GTGCGCCTCA
 801  CCAGAACCAG TTAAGAGACA ACTATCAATT CTTGAGACCC AAATTATAAG
 851  GGCCTGCCC TGTACTGAAG AAAAGGGGAG CACAAGGCCT TAATGGACAT
 901  TGACTTGTGA AAACGCAAAC ATGAATATGG TTGGAGAGCC CTGGATTAGG
 951  AGGGTGACAT GGGGAAGGCA GAGGCTGGCA CGATGGTGAC TGCCACATAA
1001  TAAAGTGGTG ATTTGGATTT TGNAAAAA
```

Fig. 5

GENE ASSOCIATED WITH SUPPRESSION OF TUMOR DEVELOPMENT

Pursuant to 35 U.S.C. §202(c), it is hereby acknowledged that the U.S. Government has certain rights in the invention described herein, which was made in part with funds from the National Institutes of Health.

FIELD OF THE INVENTION

The present invention relates to diagnosis and treatment of neoplastic disease. In particular, this invention provides a novel gene, OVCA1, the disruption of which is associated with cellular proliferation and tumor development. The OVCA1 gene provides a biological marker for early diagnosis of metastatic disease and may be useful in gene replacement therapy for treating various forms of cancer.

BACKGROUND OF THE INVENTION

The molecular basis of cancer has been the subject of a massive research effort over the past several years. Through this effort, it has been discovered that abnormal cellular proliferation results not only from activation of oncogenes, but from disruption of certain genes whose function appears to be important in maintaining normal cell division. As a well-known example, mutations in the p53 tumor suppressor gene are common in human cancer and can be identified in about half of all cases (see Harris, Science 262: 1980–1981, 1993).

Important regulatory genes such as p53 are often identified by mapping rearrangements or deletions of chromosomes that correlate with the occurrence of a particular type of cancer. The molecular genetic basis of breast cancer and ovarian cancer has been elucidated in part in this manner. Although certain oncogenes are amplified and/or overexpressed, the inactivation of multiple tumor suppressor genes appears to be important in the etiology of breast and ovarian cancers, as evidenced by observed allelic losses for polymorphic DNA markers on nearly every chromosome arm. Rearrangements or deletions of chromosome 17 are the most frequently observed changes identified in ovarian and breast cancer tumors.

One strategy for locating putative suppressor genes is to survey tumors for high rates of loss of heterozygosity ("LOH"). Combined data from four separate allelotyping studies of ovarian cancers revealed that greater than 30% of the tumors analyzed showed LOH on chromosome 6, 9, 13q, 17, 18q, 19p, 22q and Xp, with the highest LOH rates on 17q (q21, q22–q23), 17p (p13.3, 13.1), 18q (q21.3-qter, distal 2DCC), 6q (q26–q27), 11q (q23.3-qter), and 11p (p13–p15.5), in descending order. 17p, 17q, 6q, 18q and 11p are frequently deleted in breast carcinomas as well, continuing the genetic parallels between the two cancer sites.

Non-random chromosomal deletions and loss of heterozygosity of a segment of the genome are considered indicative of the presence of a tumor suppressor gene in that region. On the basis of these and other studies of breast and ovarian cancer tumors, it has been suggested that multiple loci on chromosome 17 may be important in the etiology of these diseases. Recent studies (Miki et al., Science 266: 66–71, 1994) have resulted in the identification of the BRCA1 gene, which is responsible for a portion of breast cancer and the majority of ovarian cancer cases caused by inherited susceptibility. Initial studies have indicated however that BRCA1 appears to play little or no role in common, non-hereditary forms of breast and ovarian cancer, suggesting that the genetic basis for more than 90% of cancers of the breast and ovary is still unknown (see Futreal et al., Science 266: 120–122, 1994).

Chromosome 17 has a number of additional potential cancer causing genes, including TP53 at 17p13.1 the BRCA1 gene 17q21, and genes nearby, such as prohibitin and NM23 with plausible tumor suppressor characteristics, and the proto-oncogene cERBB2. Mutations inactivating the tumor suppressing potential of the TP53 gene have also been reported in sporadic breast and ovarian cancer. However, two studies reported a high frequency of LOH on 17p in breast tumors possessing wild-type TP53 (Coles et al., Lancet 336: 761–763, 1990; Cornelis et al., Cancer Res. 54: 4200–4206 1994). It has been shown recently that alterations at 17p13.3 may be an important early event in stage 1 ovarian carcinomas and tumors of low malignant potential. In low malignant potential tumors, allelic losses at 17p13.3 were not accompanied by LOH at TP53, suggesting a more distal suppressor gene and that loss of this gene's function is required for early tumorigenesis. This same region shows frequent loss of heterozygosity in breast cancers, small-cell lung cancers, colon cancers, primitive neuroectodermal tumors, carcinoma of the cervix uteri, medulloblastoma, and astrocytoma, suggesting that a tumor suppressor gene(s) residing on chromosome 17p13.3 is involved in the development of many types of cancers.

Ovarian cancer is the fifth leading cause of cancer-related deaths among women in the United States and the most lethal gynecologic malignancy. Furthermore, more than two-thirds of the women with ovarian cancer are diagnosed with advanced disease when existing therapeutic measures are often ineffective. Breast cancer is one of the most common and important diseases affecting women. Survival rates of breast cancer patients are highest among patients with early stage disease confined to the breast without axillary lymph node involvement.

At present, there are no effective presymptomatic clinical signs or biomarkers of susceptibility to ovarian cancer or breast cancer, making early detection a high priority in medical management of the disease. Efforts to discover prognostic indicators have sought correlations between clinical pathological data and various biochemical parameters. Survival of cancer, whether of the breast, ovaries or another target, is increased through recognition of individuals who are at high risk of a disease, as well as early detection, since current therapeutic strategies for early stage disease have a higher cure rate than for diseases at later stages. For this reason, the identification of molecular markers of oncogenesis will assist in early diagnosis as well as prognostic monitoring of ongoing disease. Furthermore, if such molecular markers comprise mutations or deletions of genes essential for maintaining normal cellular division, such genes may also be developed as therapeutic agents to treat malignant disease.

SUMMARY OF THE INVENTION

In accordance with the present invention, a recombinant DNA molecule is provided which comprises a DNA segment from human chromosome 17p13.3. The DNA segment is at least 20 kilobase pairs in length. In a preferred embodiment, the DNA is isolated from human placental DNA and includes locus D17S28 of chromosome 17p13.3. This segment comprises a gene, referred to herein as OVCA1, the disruption of which is associated with malignant cell growth.

As is typical of many eucaryotic genes, the OVCA1 gene is composed of several exons and introns. The exons of the OVCA1 gene form an open reading frame which has a sequence that encodes a 71 kDa polypeptide, about 640–650 amino acids in length. In a preferred embodiment, the open reading frame encodes an amino acid sequence substantially the same as Sequence I.D. No. 2, set forth in FIG. 2. In a particularly preferred embodiment, the cDNA comprises Sequence I.D. No. 1, also shown in FIG. 2. The recombinant DNA molecule of the invention may further comprise an additional exon having a sequence substantially the same as Sequence I.D. No. 3, shown in FIG. 5.

According to another aspect of the present invention, an isolated nucleic acid molecule is provided, which comprises an open reading frame of a gene located on human chromosome 17p13.3, the gene occupying a segment of that chromosome, at least twenty kilobase pairs in length. In preferred embodiments of the invention, this nucleic acid molecule comprises a cDNA sequence such as: (1) Sequence I.D. No. 1; (2) a sequence hybridizing with part or all of Sequence I.D. No. 1, and encoding a polypeptide substantially the same as part or all of the polypeptide encoded by Sequence I.D. No. 1; and (3) a sequence encoding part or all of a polypeptide having amino acid Sequence I.D. No. 2. Oligonucleotides that specifically hybridize with portions of the OVCA1 gene or OVCA1 open reading frame described above are also provided.

According to another aspect of the present invention, a polypeptide is provided that is produced by expression of isolated nucleic acid molecule comprising part or all of an open reading frame of gene located on human chromosome 17p13.3, the gene occupying a segment of the chromosome at least 20 kb pairs in length. In a preferred embodiment, this polypeptide comprises an amino acid sequence substantially the same as part or all of sequence I.D. No. 2.

According to another aspect of the present invention, antibodies are provided that are immunologically specific for the aforementioned polypeptide or fragments thereof.

The OVCA1 gene, along with its encoded protein and antibodies thereto, provide a much-needed molecular marker for oncogenesis that will assist in early diagnosis and prognostic monitoring of malignant disease, particularly breast cancer and ovarian cancer. The gene also will be useful in gene replacement therapy or for the development of other therapeutic agents to treat various forms of malignant disease.

BRIEF DESCRIPTION OF THE DRAWINGS

FIG. 2. Nucleotide (Sequence I.D. No. 1) and predicted amino acid (Sequence I.D. No. 2) sequences for the OVCA1 cDNA and flanking regions. The predicted amino acid sequences are shown above in the three-letter code. Numbers in the left and right margins correspond to the respective nucleotide and amino acid sequences. The OVCA1 amino acid sequence shown begins at the putative NH2-terminal methionine (nucleotide 1) and ends at nucleotide 1943. The underlining of nucleotides 2154–2159 indicates the putative polyadenylation signal. The sequence shown was obtained from cDNA clones fb67-1 and 77-1, and cosmid clone 7-2, which were isolated from a human fetal brain cDNA and a human placental genomic library, respectively.

FIG. 4. Comparison of the predicted amino acid sequence of the OVCA1 protein with the S. cerevisiae chromosome IX cosmid 9150 (Sequence I.D. No. 4) and Caenorhabditis elegans cosmid C14B1 (Sequence I.D. No. 5) predicted proteins. Arrows above sequence indicate the approximate position of OVCA1 introns.

FIG. 5. Nucleotide sequence of OVCA2 (Sequence I.D. No. 3).

DETAILED DESCRIPTION OF THE INVENTION

Figure 1:
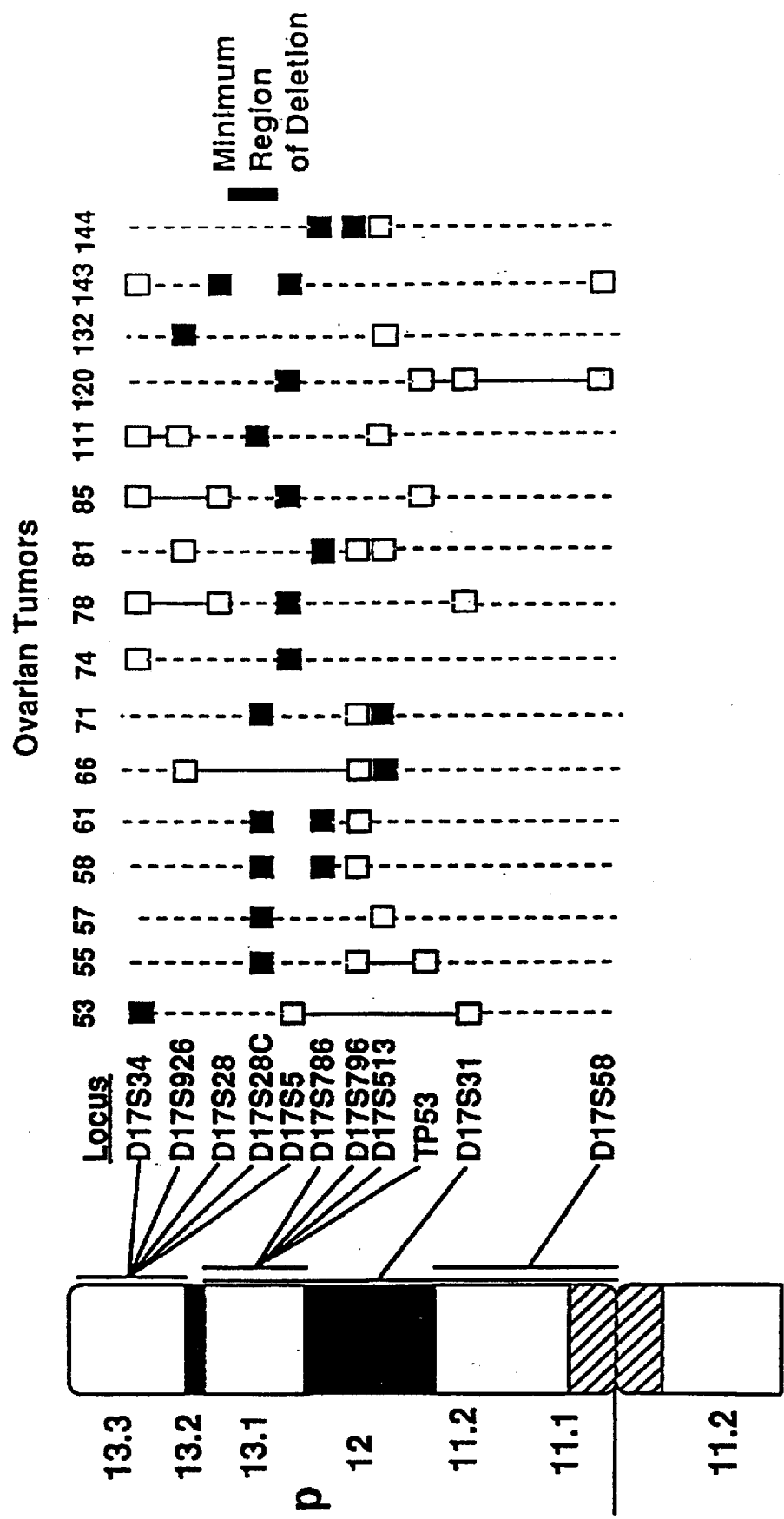
FIG. 1. Allelic deletion patterns of ovarian tumors for the short arm of chromosome 17. DNA samples from normal blood and ovarian tumor tissue were typed with STRPs on 17p. For each tumor, all informative loci are shown. Blackened squares represent constitutional heterozygosity with LOH; open squares, constitutional heterozygosity with no LOH; blank spaces, homozygous. With the assumption that alleles in all regions between loci showing allelic loss are lost, solid lines indicate retained regions of chromosome 17q and open areas show regions of allelic loss. Dashed lines represent regions that are uncertain in tumors with loss of heterozygosity for some loci.

In accordance with the present invention, a new gene from human chromosome 17 has been isolated, which appears to be involved in suppression of tumor development in at least two forms of cancer. This gene, referred to herein as OVCA1 (Ovarian Cancer 1 gene), maps to 17p13.3 and is mutated in a number of tumors and tumor cell lines. Northern blot analysis revealed that a 2.3 kb OVCA1 mRNA is expressed in normal surface epithelial cells of the ovary, but is significantly reduced or is undetectable in 90% (11 of 13) ovarian tumors and tumor cell lines analyzed. Moreover, analysis of fresh ovarian tumors and tumor cell lines has revealed a number of potential cancer-causing mutations in OVCA1 in both tumors and cell lines. These mutations were not detected in patients' matching lymphocyte DNA, suggesting that these alterations resulted from acquired somatic mutations and therefore are not likely to be random polymorphisms. These initial data are consistent with the classification of OVCA1 as a tumor suppressor gene.

The OVCA1 gene spans approximately 20 kb of DNA in chromosome 17p13.3, and is composed of 13 exons. The OVCA1 exons form an open reading frame that encodes a protein of about 648 amino acids with a predicted molecular weight of approximately 71 kDa. The OVCA1 cDNA (Sequence I.D. No. 1) and corresponding deduced amino acid sequence (Sequence I.D. No. 2) are shown in FIG. 2. In addition, a nucleic acid that represents a unique exon, positioned in the intron between exon 12 and 13 of OVCA1, has been isolated. This sequence (Sequence I.D. No. 3) is referred to as OVCA2 and is shown in FIG. 5.

Sequence comparisons of cDNA clones of OVCA1 and OVCA2 and their predicted proteins (using Genbank/EMBL and Swissplot databases) revealed sequence identity (at the amino acid level) to predicted proteins of unknown function, from Caenorhabditis elegans Cosmid c14B1 and the Saccharomyces cerevisiae chromosome IX cosmid. High-stringency southern blotting of DNA samples from several different mammalian species with OVCA1 revealed strongly hybridizing fragments in all species examined (see Example 1 for stringency conditions).

The OVCA1 gene having the cDNA represented by Sequence I.D. No. 1 was isolated by using a number of deletion mapping and positional cloning methods, as described in Example 1. Allelic variants and natural mutants of Sequence I.D. No. 1 (as well as Sequence I.D. Nos. 2 and 3) are likely to exist within the human genome and within genomes of other species. Because such variants are expected to possess certain differences in nucleotide and amino acid sequence, this invention provides an isolated nucleic acid molecule and its encoded protein, having at least about 50–60% (preferably 60–80%, most preferably over 80%) sequence homology in the coding region with the nucleotide sequences set forth as Sequence I.D. No. 1 or No. 3 (and, preferably, specifically comprising the coding region of Sequence I.D. No. 1 or No. 3), and the amino acid sequence of Sequence I.D. No. 2. Because of the natural sequence variation likely to exist among OVCA1 genes and their encoded proteins, one skilled in the art would expect to find up to about 40–50% variation in the coding sequence, while still maintaining the unique properties of the coding sequence and the encoded protein of the present invention. Such an expectation is due in part to the degeneracy of the genetic code, as well as the known evolutionary success of conservative amino acid sequence variations, which do not appreciably alter the nature of a protein. Accordingly, such variants are considered substantially the same as one another and are included within the scope of the present invention. Of course, the introns of the OVCA1 gene are likely to possess even greater sequence variation, in keeping with the known variability of introns in eucaryotic genes.

For purposes of this invention, the term "substantially the same" refers to nucleic acid or amino acid sequences having sequence variations that do not materially affect the nature of the protein (i.e., the structure and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conserved substitute amino acids in the encoded polypeptide. With reference to amino acid sequences, the term "substantially the same" refers generally to conservative substitutions and/or variations in regions of the polypeptide not involved in determination of structure or function.

Persons skilled in the art will appreciate that nucleotide sequences having sufficient homology (as discussed above) to be considered "substantially the same" are often identified by hybridization to one another under appropriate hybridization conditions. Identification and isolation of nucleic acids of the invention by hybridization under various stringency conditions is described in greater detail below.

The following description sets forth the general procedures involved in practicing the present invention. To the extent that specific materials are mentioned, it is merely for purposes of illustration and is not intended to limit the invention. Unless otherwise specified, the general cloning procedures, such as those set forth in Sambrook et al., *Molecular Cloning*, Cold Spring Harbor Laboratory (1989) (hereinafter "Sambrook et al.") are used.

I. Preparation of OVCA1 nucleic acid molecules, encoded proteins and antibodies thereto A. Nucleic Acid Molecules Nucleic acid molecules comprising part or all of the OVCA1 gene of the invention may be prepared by two general methods: (1) they may be synthesized from appropriate nucleotide triphosphates, or (2) they may be isolated from biological sources. Both methods utilize protocols well known in the art.

The availability of nucleotide sequence information, such as Sequence I.D. Nos. 1 and 3, enables preparation of an isolated nucleic acid molecule of the invention by oligonucleotide synthesis. Synthetic oligonucletoides may be prepared by the phosphoramadite method employed in the Applied Biosystems 38A DNA Synthesizer or similar devices. The resultant construct may be purified by high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a double-stranded DNA molecule several kilobases in length may be synthesized as multiple smaller segments of appropriate complementarily. Complementary segments thus produced may be annealed such that each segment possesses appropriate cohesive termini for attachment of an adjacent segment. Adjacent segments may be ligated by annealing cohesive termini in the presence of DNA ligase to construct an entire double-stranded molecule. A synthetic DNA molecule so constructed may then be cloned and amplified in an appropriate vector.

OVCA1 nucleic acid sequences may be isolated from appropriate biological sources using methods known in the art. In a preferred embodiment, a cDNA clone is isolated from an expression library of human origin. In another preferred embodiment, human genomic clones containing OVCA1 may be isolated. Alternatively, cDNA or genomic clones from other species may be obtained.

In accordance with the present invention, nucleic acids having the appropriate sequence homology with part or all of Sequence I.D. Nos. 1 or 3 may be identified by using hybridization and washing condition of appropriate stringency. For example, hybridizations may be performed, according to the method of Sambrook et al., using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37°–42° C. for at least six hour. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42°–65° in 1×SSC and 1% SDS, changing the solution every 30 minutes. In a preferred embodiment, hybridizations are performed in hybridization solution comprising 0.5M NaPO$_4$, 2 mM EDTA, 7% SDS and 0.1% sodium pyrophosphate (pH 7.1) at about 65° C. for 20 hours. For high-stringency conditions, membranes are subsequently washed sequentially for 1 hour each in: (1) 2×SSC, 0.5×SET, 0.1% sodium pyrophosphate; and (2) 0.1×SSC, 0.5×SET, 0.1% sodium pyrophosphate. For low-stringency conditions, membranes are washed at 50° C. for 30 minutes in 2×SSC, 0.5×SET, 0.1% sodium pyrophosphate.

Nucleic acids of the present invention may be maintained as DNA in any convenient cloning vector. In a preferred embodiment, genomic clones are maintained in a cosmid vector, such as pWE15 (Stratagene). In another preferred embodiment, clones are maintained in plasmid cloning/expression vector, such as pBluescript (Stratagene, La Jolla, Calif.), which is propagated in a suitable *E. coli* host cell.

OVCA1 nucleic acid molecules of the invention (including OVCA2) include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of Sequence I.D. Nos. 1 and 3 or selected intron sequences from genomic clones isolated in accordance with the present invention (such as those found in cosmid 7-2, described in Example 1). Such oligonucleotides are useful as probes for detecting OVCA1 genes (and specific mutations) in test samples, e.g. by PCR amplification, or as potential regulators of gene expression.

B. Proteins

A full-length OVCA1-encoded protein of the present invention may be prepared in a variety of ways, according to known methods. The protein may be purified from appropriate sources, e.g., human or animal cultured cells or tissues, by immunoaffinity purification. However, due to the limited amount of such a protein that may be present in a sample at any given time, particularly in tumors or tumor cell lines, conventional purification techniques are not preferred in the present invention.

The availability of the isolated OVCA1 coding sequence enables production of protein using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

Alternatively, according to a preferred embodiment, the recombinant protein may be produced by expression in a suitable procaryotic or eucaryotic system. For example, part or all of a DNA molecule, such as the cDNA having Sequence I.D. No. 1 or No. 3, may be inserted into a plasmid vector adapted for expression in a bacterial cell, such as E. coli, or into a baculovirus vector for expression in an insect cell. Such vectors comprise the regulatory elements necessary for expression of the DNA in the bacterial host cell, positioned in such a manner as to permit expression of the DNA in the host cell. Such regulatory elements required for expression include promoter sequences, transcription initiation sequences and, optionally, enhancer sequences. Production of a recombinant OVCA1 protein by expression in a procaryotic system is described in greater detail in Example 2.

The protein produced by OVCA1 gene expression in a recombinant procaryotic or eucaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

Proteins prepared by the aforementioned methods may be analyzed according to standard procedures. For example, such proteins may be subjected to amino acid sequence analysis, according to known methods.

The present invention also provides antibodies capable of immunospecifically binding to proteins of the invention. Polyclonal antibodies directed toward OVCA1-encoded proteins may be prepared according to standard methods. In a preferred embodiment, monoclonal antibodies are prepared, which react immunospecifically with various epitopes of the proteins. Monoclonal antibodies may be prepared according to general methods of Köhler and Milstein, following standard protocols. Polyclonal or monoclonal antibodies that immunospecifically interact with OVCA1-encoded proteins can be utilized for identifying and purifying such proteins. For example, antibodies may be utilized for affinity separation of proteins with which they immunospecifically interact. Antibodies may also be used to immuoprecipitate proteins from a sample containing a mixture of proteins and other biological molecules. Other uses of antibodies are described below.

II. Uses of OVCA1 Nucleic Acids, Encoded Proteins and Antibodies Thereto

As is typical of tumor suppressor genes, rearrangements and mutations in OVCA1 have been found to be associated with the tumorigenic state in tissues and cell lines. Accordingly, isolated OVCA1 nucleic acids, proteins and antibodies thereto will find wide utility as prognostic indicators of neoplastic disease and as therapeutic agents for the treatment of many types of cancer including, but not limited to cancers of the breast, lungs, colon, ovaries and cervix, and other carcinomas such as neuroectodermal tumors, medulloblastoma and astrocytoma.

A. OVCA1 Nucleic Acids

Nucleic acids comprising part or all of the OVCA1 gene may be used for a variety of purposes in accordance with the present invention. As has been done for other tumor suppressor genes, such as p53, selected OVCA1 sequences (DNA, RNA or fragments thereof) may be used as probes to identify mutations or rearrangements in a patient's DNA, and/or monitor the level of OVCA1 transcripts in tissues suspected of being malignant. As discussed earlier, mutations in OVCA1 appear to be associated with sporadic (as opposed to familial) breast cancer as well as with development of ovarian carcinomas, among others. Accordingly, early identification of disruptions in the OVCA1 gene will facilitate diagnosis of malignancies at early stages when the chance for their successful treatment is much greater. OVCA1 sequences may be utilized as probes in a variety of assays known in the art, including but not limited to: (1) in situ hybridization; (2) Southern hybridization; (3) Northern hybridization; and (4) assorted amplification reactions, such as polymerase chain reaction (PCR).

The OVCA1 nucleic acids of the invention may also be utilized as probes to identify related genes either from humans or from other species. As discussed above, high-stringency hybridization studies have shown that OVCA1 exists in other mammalian species including but not limited to cow, cat, dog, horse, mouse, pig and rat. As is well known in the art, hybridization stringency may be adjusted so as to allow hybridization of nucleic acid probes with complementary sequencing of varying degrees of homology.

As described above, the coding region of OVCA1 is also used to advantage to produce substantially pure OVCA1 encoded proteins or selected portions thereof. As described below, these proteins may also be used in diagnosis and therapy of metastatic disease.

Because OVCA1 appears to be important in maintenance of normal cell division, a preferred embodiment of the present invention involves gene therapy in which a normal OVCA1 gene or transcript is supplied to a patient having cells or tissues lacking OVCA1, or in which OVCA1 has been disrupted, for the purpose of encouraging normal growth in otherwise tumorigenic tissue. This type of gene therapy may be particularly applicable to cancers of the blood, wherein bone marrow or peripheral blood is subjected to genetic transformation protocols ex vivo, during the course of a normal autologous stem cell transplantation procedure. OVCA1 nucleic acid molecules, or fragments thereof, may also be utilized to control the expression of endogengous OVCA1 genes. If desired, the nucleic acid molecules of the invention may be used to reduce or prevent expression of OVCA1 genes in a targeted cell population. In this embodiment, antisense oligonucleotides are employed which are targeted to specific regions of OVCA1 that are critical for gene expression. The use of antisense oligonucleotides to reduce or eliminate expression of a pre-determined gene is known in the art. In a preferred embodiment, such antisense oligonucleotides are modified in various ways to increase their stability and membrane permeability, so as to maximize their effective delivery to target cells in vitro and in vivo. Such modifications include the preparation of phosphorothioate or methylphosphonate derivatives, among many others, according to procedures known in the art. This embodiment of the invention may be particularly applicable to the study of cellular proliferation and tumor development in vitro, for the purpose of elucidating the mechanism of cancer development and for developing anti-cancer drugs.

B. OVCA1-Encoded Proteins and Antibodies Thereto

The OVCA1-encoded protein, or fragments thereof, may be used to produce polyclonal or monoclonal antibodies, which also may serve as sensitive detection reagents for the presence and accumulation of the OVCA1-encoded polypeptide in cultured cells or tissues from living patients (the term "patient" refers to both humans and animals). Because the OVCA1-encoded protein has not yet been isolated from natural sources, such antibodies will greatly accelerate the identification, isolation and characterization of this protein in mammalian cells and tissues. Recombinant techniques enable expression of fusion proteins containing part or all of the OVCA1-encoded protein. The full-length protein or fragments of the protein may be used to advantage to generate an array of monoclonal antibodies specific for various epitopes of the protein, thereby potentially providing even greater sensitivity for detection of the protein in cells or tissues.

Polyclonal or monoclonal antibodies immunologically specific for the OVCA1-encoded protein may be used in a variety of assays designed to localize and/or quantitate the protein. Such assays include, but are not limited to: (1) flow cytometric analysis; (2) immunochemical localization of the protein in cultured cells or tissues; and (3) immunoblot analysis (e.g., dot blot, Western blot) of extracts from cells and tissues. Additionally, as described above, such antibodies can be used for the purification of OVCA1-encoded proteins (e.g. affinity column purification, immunoprecipitation).

From the foregoing discussion, it can be seen that OVCA1 nucleic acids, protein and antibodies thereto can be used in many ways for diagnosis and prognosis of human neoplastic diseases. However, one skilled in the art will appreciate that these tools will also be useful in animal and cultured cell experimentation with respect to various carcinomas. They can be used to monitor the effectiveness of potential anti-cancer agents on cellular proliferation in vitro, and/or to assess the development of neoplasms or other malignant diseases in animal model systems.

The following examples are provided to describe the invention in further detail. These examples are intended to illustrate and not to limit the invention.

EXAMPLE 1

Identification of OVCA1, a Candidate Tumor Suppressor Gene on Chromosome 17p13.3

Rearrangements or deletions of chromosome 17 are one of the most frequently observed changes identified in breast and ovarian tumors, among others. Molecular analysis suggests that, in addition to the BRCA1 gene on 17q21 and the TP53 gene on 17p13.1, there is at least one other tumor suppressor gene on chromosome 17 involved in the genesis of ovarian and/or breast cancer. Loss of heterozygosity (LOH) identified within regions of 17p13.3 occurs frequently in ovarian tumors which express wild type TP53. This example describes the use of deletion mapping and positional cloning methods to identify a novel gene, OVCA1 (ovarian cancer 1 gene) that maps to 17p13.3, and is mutated in a number of tumors and tumor cell lines.

MATERIALS AND METHODS

Isolation of DNA and RNA from Tumors and Matched Blood Samples. Preparation of RNA for Northern blotting, and DNA isolation for LOH and SSCP analysis is by methods described in Godwin et al., Am. J. Hum. Genet. 55: 666–677 (1994).

cDNA cloning. Human cDNA libraries derived from an ovarian cancer cell line, A2780, a cervical cancer cell line, HeLa, normal thymus (Stratagene), and fetal brain (Stratagene) were screened by probing with conserved genomic fragments of cosmid 7-2 (described below). Membranes were hybridized at $1.5 \times 10^6$ cpm/ml of hybridization solution (0.5M $NaPO_4$, 2 mM EDTA, 7% SDS, and 0.1% sodium pyrophosphate (NaPPi), 65° C. for 20 hours. The membranes were sequentially washed at high stringency, i.e., 65° C. for 1 hour in 2×SSC, 0.5×SET (1×SET is 1% SDS, 5 mM EDTA, 10 mM Tris-HCl), 0.1% NaPPi; and 0.1×SSC, 0.5×SET, 0.1% NaPPi, respectively. Washed membranes were exposed to Kodak XAR-5 film with a Lightning Plus intensifying screen (NEN-Dupont) at −70° C. DNA probes containing repetitive sequences were pre-annealed using human placental (Sigma, St. Louis, Mo.) and Cot-1 (Bethesda Research Laboratories, Gaithersburg, Md.) DNA prior to hybridization. Positive clones were obtained by screening roughly one million plaques from an oligo(dT)-primed fetal brain cDNA library constructed in pBlueScript (Stratagene) by hybridization with a 1.6 kbpEcoRI fragment of cosmid 7-2 as probe.

For low-stringency Southern hybridizations, membranes were hybridized as above, but were washed at 50° C. for 30 min. in 2×SSC, 0.5×SET, 0.1% NaPPi. Washed membranes were exposed to Kodak XAR-5 film with a Lightning Plus intensifying screen (NEN-Dupont) at −70° C. DNA probes containing repetitive sequences were pre-annealed using human placental (Sigma, St. Louis, Mo.) and Cot-1 (Bethesda Research Laboratories, Gaithersburg, Md.) DNA prior to hybridization.

Single Strand Conformational Polymorphism (SSCP) Analysis. PCR was carried out in a reaction volume of 10 ml containing 100 ng of genomic DNA template, 10 mM tris-HCl pH 8.3, 50 mM KCl, 1.5 mM $MgCl_2$, 0.001% gelatin, 1 mM each of forward and reverse primer, 60 mM each dATP, dGTP, dCTP, and dTTP, 0.1 mCi [$\alpha$-$^{32}$P]-dATP (DuPont, NEN), 5% dimethyl sulfoxide (DMSO), and 0.5 U Amplitaq DNA polymerase (Perkin Elmer). Following an initial denaturation step at 94° C. for 4 minutes, DNA was amplified through 20 cycles consisting of 1 minute denaturing at 94° C., 1 minute annealing at 68° C.–0.5° C./cycle and 1 minute extension at 72° C. The samples were then subjected to an additional 25 cycles, consisting of 1 minute denaturation at 94° C., 1 minute at 58° C., and 1 minute extension at 72° C., and a final extension at 72° C. for 5 minutes.

PCR reaction products were diluted 1:10 in denaturing loading dye (95% formamide, 10 mM NaOH, 0.25% bromophenol blue, and 0.25% xylene cyanol), heated at 94° C. for 5 minutes, and flash cooled on ice. Four microliters were loaded onto a 0.5×MDE gel (AT Biochem) prepared according to the manufacturer's specifications, and run at 5 watts for 12–16 hours at room temperature in 0.6×TBE (1×= 0.09M Tris, 0.09M boric acid, 0.002M EDTA). Following electrophoresis, the gel was dried and exposed to autoradiography film at −80° C. for 1–12 hours. Variant and normal SSCP bands were cut out from the gels after alignment with the autoradiograph, and the DNA eluted in 100 μl of ddH₂O at 37° C. for 3 hours.

DNA Sequencing. Sequencing was performed on double stranded plasmid DNA using the dideoxy method, with SK, KS or primers derived from obtained sequences (See Table 2). For direct sequencing of the variant SSCP bands, 2 μl of the eluted DNA was used as template for secondary PCR reactions carried out using the conditions described above, except radiolabelled dATP was omitted. Following amplification, the DNA was collected on Wizard resin (Promega), eluted in 50 μl of ddH₂O, and the purified PCR product was subjected to cycle sequencing using the fmol DNA Sequencing System (Promega).

PCR analysis of simple tandem repeat polymorphisms. Simple tandem repeat polymorphisms (STRPs) were typed in a PCR based assay containing 15–30 ng of genomic DNA, 10 mM Tris-HCl pH 8.3, 50 mM KCl, 1.5 mM MgCl₂, 0.001% gelatin, 0.4 μM of each primer, dCTP, dGTP, and TTP each 16 μM, dATP at 2 μM, 0.65Ci [α-³⁵S]-dATP (DuPont, New England Nuclear), 5% DMSO, and 0.25 U Amplitaq DNA polymerase (Perkin Elmer) in a final volume of 5 μl. Alleles were amplified as described above. PCR reaction products were diluted 1:1 in loading buffer (90% formadmide, 20 mM ETDA, 0.3% bromophenol blue, 0.3% xylene cyanol), denatured at 94° C. for 5 minutes and loaded (4 μl) onto a 6% denaturing polyacrylamide gel, then electrophoresed at 90 watts in 1×TBE. After electrophoresis, gels were dried at 70° C. under vacuum, and exposed to Kodak XAR 5 film for 24–28 hours.

RESULTS

Interstitial deletions are helpful in defining the smallest region of overlapping deletion in which a tumor suppressor gene may be found. Previous studies have reported that sporadic ovarian tumors of low malignant potential and low-stage carcinomas have allelic loss at chromosome 17p13.3, whereas TP53 at 17p13.1 and the BRCAL locus at 17q21 are retained. Using DNA isolated from 150 ovarian tumors, a panel of polymorphic DNA markers was evaluated for LOH on 17p. A detailed deletion map of cases showing limited LOH on 17p revealed a common region of deletion, distal to YNH37.3 (D17S28) and proximal to YNZ22 (D17S5), which spans less than 20 kilobase pairs (kbp) and is located on chromosome 17p13.3 (FIG. 1).

Cosmid clones surrounding and including the two loci were isolated from a human placental DNA cosmid library constructed in vector pWE15 (Stratagene). Several strategies were employed to evaluate these clones for potential expressed sequences. First, DNA fragments were evaluated for potential growth suppressor function. We introduced by transfection cosmid clones containing genomic inserts spanning the limited region of deletion and a selectable marker (Neoʳ) and evaluated clonal outgrowth in the presence of geneticin. Of the cosmids tested, clone pWE15/7-2, containing approximately 40 kbp of genomic DNA, was the most effective at suppressing colony formation. Cosmid clone pWE15/7-2 was deposited on Dec. 2, 1995 with the American Type Culture Collection and assigned ATCC Accession No. 97331. Next, clone 7-2 was evaluated using exon amplification methods. A 101 bp exon was identified, which mapped to a 1.6 kbp EcoRI DNA fragment of clone 7-2. Hybridization of the 101 bp fragment a low stringency (see Materials and Methods) to a "zoo" blot (see below) revealed conservation among other mammals. Sequencing of the 1.6 kb EcoRI fragment revealed a second potential open reading frame 150 bp away from the putative 101 bp exon.

Four human cDNA libraries, derived from an ovarian cancer cell line, cervical cancer cell line, normal thymus, and fetal brain were screened at high stringency (see Materials and Methods) using the 1.6 kbp EcoRI fragment as a probe. Several positive clones were isolated from the human fetal brain cDNA library constructed in a pBluescript vector (Stratagene). Only two of the clones (fb67-1 and 77-1) hybridized to any of the clones of the 17p13.3 cosmid "contig", indicating the presence of a potential family of genes at loci other than 17p13.3. Related OVCA1 clones isolated from the fetal brain cDNA library were labeled as follows: fb50-1-1, fb52-1-1, fb53-1-1, fb57-1-1, fb63-1-1, fb69-1-1 and fb73-1-1. Partial sequence analysis of these clones has been performed. Other clones that have not been sequenced include fb43-1-1, fb43-2-1 and fb-46-1-1. Because the aforementioned clones were isolated by hybridization with a segment of cosmid clone 7-2 (containing part of Sequence I.D. No. 1), the clones are considered to be "substantially the same" as their corresponding sequences in Sequence I.D. No. 1, within the scope of the present invention.

Sequence analysis of clones fb67-1 and fb77-1 revealed a consensus of 2159 bp (zero bp of the 5'-untranslated, 1920 bp of coding region and 239 bp of the 3'-untranslated region). Identification of a presumptive initation codon flanked by sequences resembling the Kozak consensus sequence was accomplished using an "achored" PCR method (Rapid Amplification of cDNA Ends, Gibco/BRL). Thirty-five additional nucleotides were identified, including 18 bases of the 5'-untranslated region and two potential initation codons. The reading frame using the first AUG encodes a protein of 648 amino acids with a predicted molecular weight of about 71 kDa (FIG. 2). Using the second AUG codon, the predicted protein is about 643 amino acids long with a predicted molecular weight of about 70 kDa. A polyadenylation signal was observed 18bp upstream from the polyadenylation site (FIG. 2). Northern blot analysis, using the 5'-portion of the fb77-1 cDNA insert as probe, detected a 2.3 kb transcript of RNA from ovarian surface epithelial cells. A plasmid containing this cDNA insert, which encodes OVCA1, has been deposited with the ATCC under the terms of the Budapest Treaty. The plasmid has been given ATCC designation No. 209189. The length of the cDNA plus 150–200 bp of poly(A) tail probably account for the entire length of the transcript detected in northern blot analysis.

Genomic DNA samples from several different species were also probed with a full-length OVCA1 cDNA fragment. High stringency blots (see Materials and Methods) revealed strongly hybridizing fragments in tissue from human, cow, cat, dog, horse, mouse, pig, and rat. These results suggest that OVCA1 is highly conserved in mammals.

Figure 4:
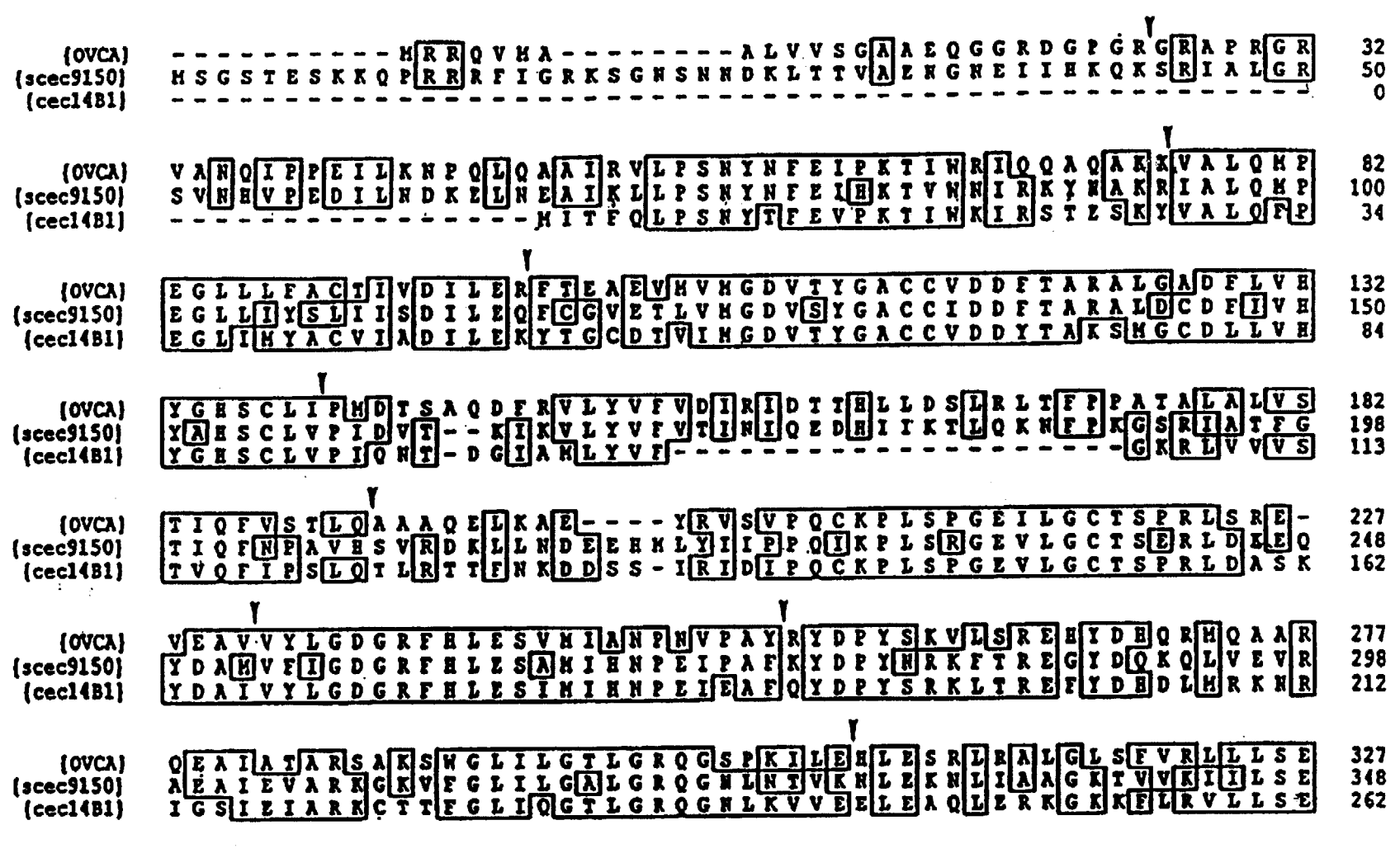
Figure 4:
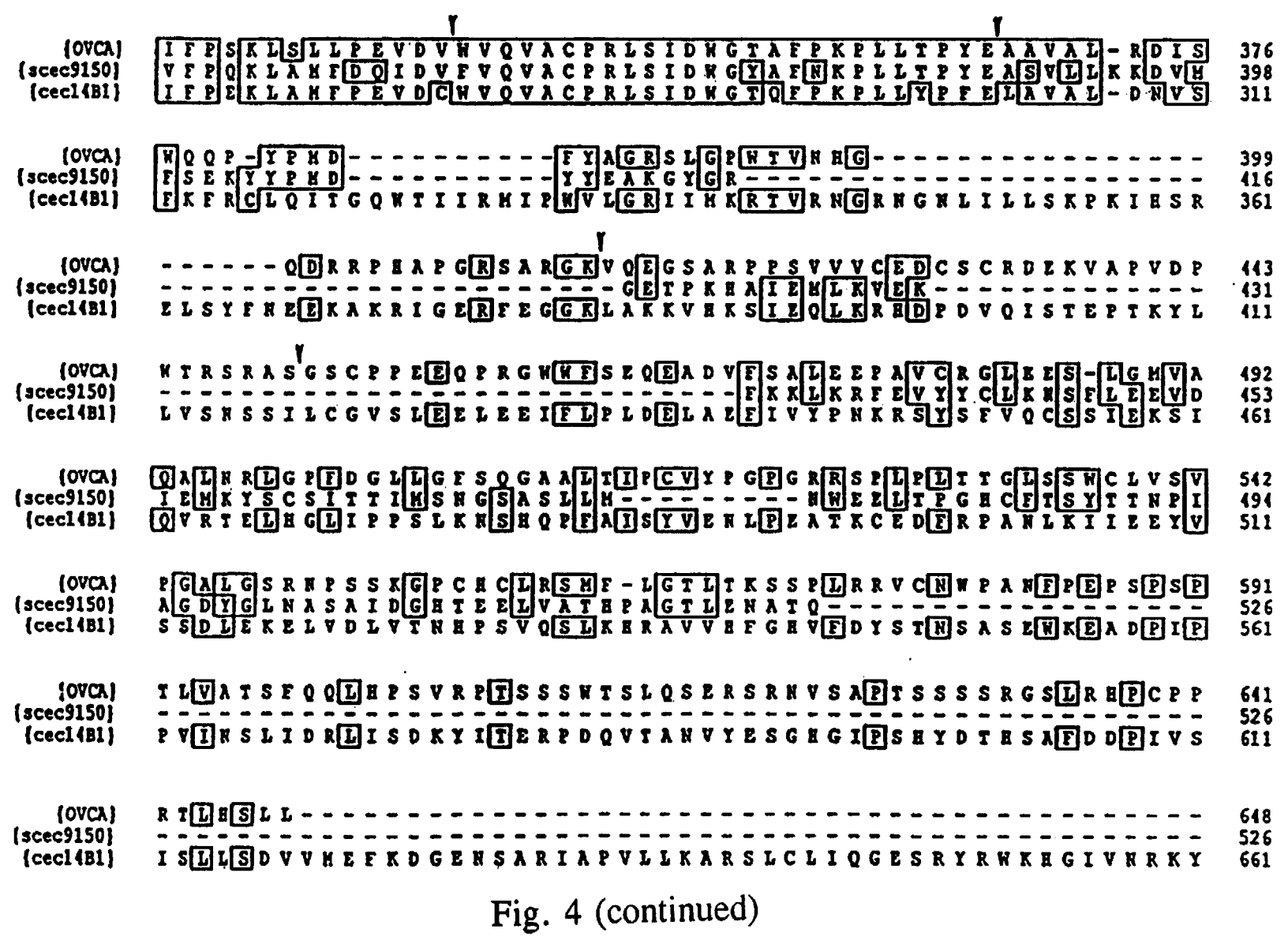

BLAST searches of the Genbank/EMBL and Swissplot databases, respectively, revealed extensive sequence identity (both at the nucleotide or the amino acid level) to two recently identified sequences: S. cerevisiae chromosome IX cosmid 9150 and Caenorhabditis elegans cosmid C14B1 (FIG. 4). The predicted gene product of OVCA1 showed significant sequence similarity over 315 and 375 of the 648 amino acid residues (51% and 44% identity) when compared to the yeast and nematode proteins, respectively. The function of these two predicted proteins is unknown at present time; the sequences were identified as the result of yeast and nematode genome sequencing projects.

Figure 3:
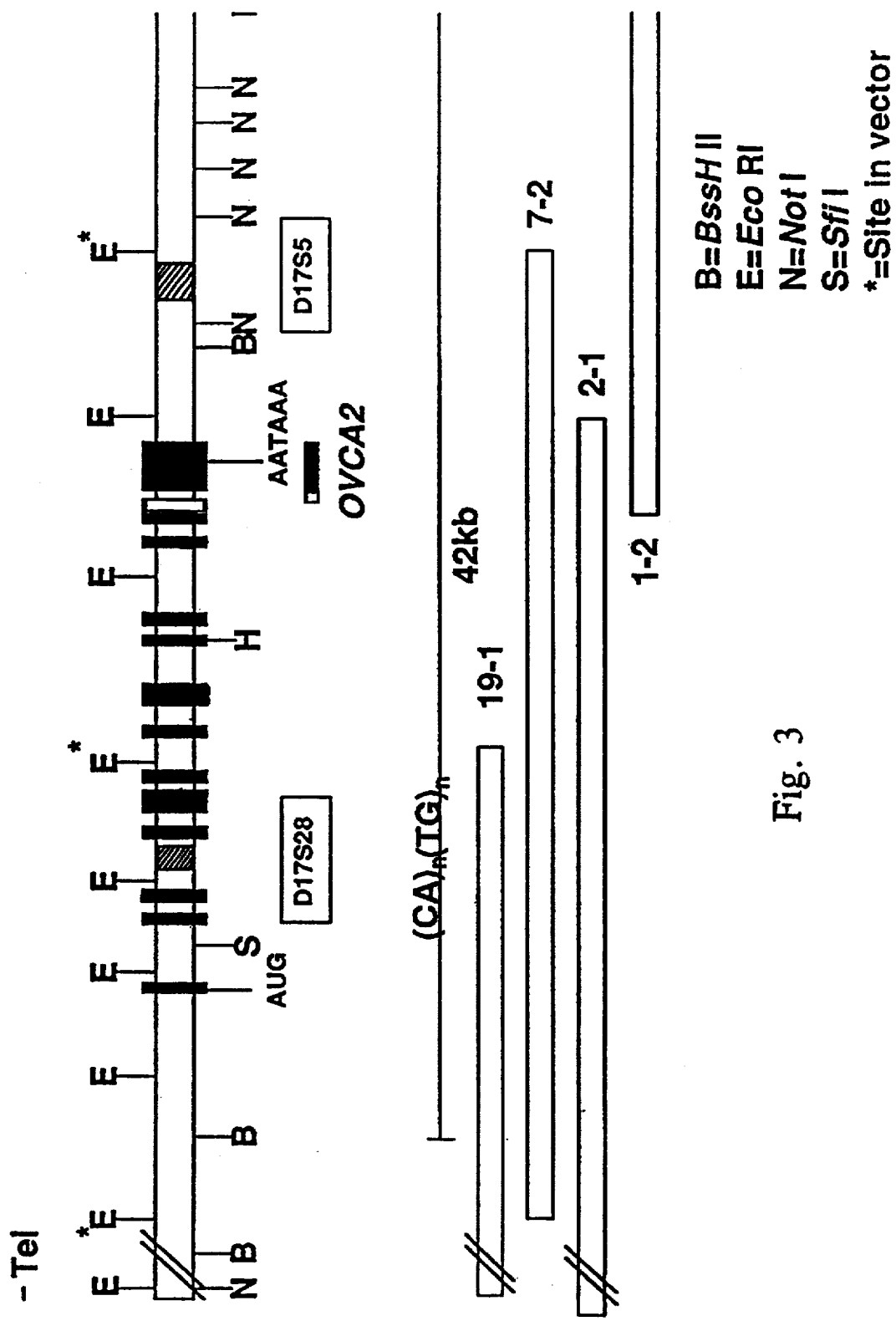
FIG. 3. Schematic diagram of chromosome 17p13.3 containing the OVCA1 gene. Black rectangles correspond to the open reading frames of OVCA1 and white rectangle corresponds to the first exon of OVCA2. Cosmid clones, used to identify OVCA1 and 2, which span the minimal region of deletion in ovarian cancer are indicated. Hatched areas denote locations of loci D17S28 and D17S5.

Restriction mapping of genomic clones using cDNA probes and sequence comparison between cDNA and genomic clones indicated that OVCA1 consists of 13 exons, which span approximately 20 kbp of genomic DNA. The entire OVCA1 cDNA sequence is present in the insert of cosmid 7-2. The position of the 13 exons relative to the common region of deletion defined by DNA markers D17S28 and D17S5 is shown in FIG. 3.

Hybridization of RNA blots to a labeled fragment of the entire fb77-1 cDNA insert revealed two distinct transcripts of 2.3 kb and 1.1 kb. The two transcripts are readily detected in all tissue examined at similar levels. Northern blot analysis reveals that the 2.3 kb OVCA1 mRNA is expressed in normal surface epithelial cells of the ovary, but the level of the 2.3 kb transcript is significantly reduced or is undetectable in a majority (11/13) of the ovarian tumors and tumor cell lines. We have also cloned the smaller transcript and have found that it is composed of exon 13 of OVCA1 and a unique exon positioned in the intron between exon 12 and 13 of OVCA1. We refer to this transcript as OVCA2 (FIG. 5). A plasmid containing the cDNA encoding OVCA2 has been deposited With the ATCC under the terms of the Budapest Treaty. The plasmid has been given ATCC designation No. 209190.

Ovarian carcinomas were typed for LOH, using four highly polymorphic simple tandem repeat markers: D17S926, D17S796 which lie distal to OVCA1 and D17S786, D17S513, which lie proximal to OVCA1. Thirty-seven of 68 (54%) informative ovarian tumors exhibited LOH frequencies consistent with previous measurements. This panel, plus 32 additional ovarian tumors (LOH status undetermined) were examined for OVCA1 mutations. The panel represents Caucasian, Hispanic, and African American patients of varying ages (Table 1).

TABLE 1

Age of ovarian cancer onset and race of patients studied. FCCC, Fox Chase Cancer Center, LH, Lankenau Hospital, GOG, and Gynelogic Oncology Group; Cau, Caucasian, H, Hispanic, Af Am, African American.

| | AGE | | RACE | | |
|---|---|---|---|---|---|
| | 45 or under | Over 45 | Cau | H | Af Am |
| FCCC | 5 | 53 | 56 | 0 | 2 |
| LH | 7 | 20 | 22 | 0 | 5 |
| GOG | 15 | 40 | 43 | 5 | 7 |

The complete coding region and intron-exon boundary sequences of OVCA1 was screened in this tumor set by a combination of single-strand conformation polymorphism (SSCP) analysis and direct sequencing. Based on genomic sequence analysis, polymerase chain reaction (PCR) primers were designed to screen the complete coding region (1944) and intron-exon boundaries of OVCA1. Since exon 13 is too large (831 bp) to analyze effectively in one piece by SSCP, three overlapping primer sets were designed for this exon, each with a length of 200–350 bp (Table 2).

TABLE 2

Oligonucleotide primers for OVCA1
(Numbers in parentheses are Sequence I.D. Nos.)

| | 5'-primer | 3'-primer |
|---|---|---|
| exon1 | CGCCCCTATCTCCTCCTTTA (6) | TGGTCCTGTCCCTAACTTGG (7) |
| exon2 | CATCTCAATCTGGCTTCAGC (8) | AACCCCAGCTCAATGATCAC (9) |
| exon3 | CTAGCCCTCCACCTCTCAT (10) | AGCCTGGCTCACCCTCCT (11) |
| exon4 | AGGGTGGGTCTCTCCTAC (12) | ATGGGGAAGATGAATGTG (13) |
| exon5 | CCTCTGCTGCTCCTACCT (14) | TGTCCACCCTACAGGAGG (15) |
| exon6 | CTCTCCTGCCCCAGCCGTTGG (16) | GATGAACCTAAGACTCCCTCC (17) |
| exon7 | CTTCTGCTGCCCTAAACCAC (18) | AGTGGCAGGGAATCTCACC (19) |
| exon8 | CTGAGTCAGGATCTGTGTGCA (20) | TGTTCCCAGTCACTTCCCTC (21) |
| exon9 | TAGGCCACAGGTTCAGCTTT (22) | CAGCCTTCAAGACGAGCTG (23) |
| exon10 | CACTGTCACGTTCTTCAGCA (24) | ACCCCACTCCACTCCAGAC (25) |
| exon11 | ACACTGGCAGATGTTATTGTCC (26) | CTCCTCCCTCCTGGAAGC (27) |
| exon12 | GGAGGGAAACGCAGGGTC (28) | AGGCGTTCCCATGACAAC (29) |
| exon13a | GAGGCTGGTGGTTTTCAGAGC (30) | GGGACAGAAACTAGACACCAAG (31) |
| exon13b | GGGTTTATCCTCTTGGTGTCT (32) | CATTTCTTGATCTTTCACTCT (33) |
| exon13c | TGGACCAGTTTGCAGAGTGA (34) | TATGTGGCAGTCACCATCGT (35) |

Preliminary studies of 100 fresh ovarian tumors (primarily high grade and late stage) and 13 tumor cell lines for mutations in OVCA1 has revealed a number of potential cancer-causing mutations in both tumors and cell lines (Table 3).

TABLE 3

Mutations in OVCA1.

| Patient # | Location | Codon | Mutation | Result |
|---|---|---|---|---|
| GOG19 | int3 | | A–G | Unknown |
| OVCAR4 | ex4 | 138 | G–T | Splicing error |
| OVCAR4 | ex4 | 105 | G–C | Met105Ile |
| A2780/4E | int4 | | G–A | Splicing error |
| 1A9 | ext4 | 102 | G–A | Ala102Thr |
| GOG4 | int4 | | G–A | Splicing error |
| GOG25 | int4 | | T–A | Splicing error |
| GOG40 | int4 | | C–A | Splicing error |
| UPN61 | ex4 | 99 | C–G | Phe99Leu |
| UPN92 | int4 | | C–G | Unknown |
| UPN106 | ex4 | 105 | A–G | Met105Val |
| UPN123 | ex4 | 105 | A–G | Met105Val |
| CP70 | ex8 | 298 | G–C | Gly298Ala |
| UPN62 | ex9 | 329 | insC | Frameshift |
| UPN96 | ex13 | 563 | G–T | Met563Arg |

A total of fifteen mutations, many in the introns flanking exon 4, have been detected. Moreover, these mutations are not detected in the patients' matching lymphocyte DNA, suggesting that these alterations are the result of acquired somatic mutations and are therefore not likely to be random polymorphisms. Multiple common and rare polymorphisms were also identified in the OVCA1 coding sequence (Table 4) and were used to directly assess the frequencey of LOH for OVCA1.

TABLE 4

Polymorphisms in OVCA1

| Exon | Codon Location | Base in Codon | Nucleotide Change | Result |
|---|---|---|---|---|
| 1 | 7 | 2 | C–T | Ala–Val |
| 2 | 32 | 2 | C–A | Ala–Asp |

TABLE 4-continued

Polymorphisms in OVCA1

| Exon | Codon Location | Base in Codon | Nucleotide Change | Result |
|---|---|---|---|---|
| 4 | 104 | 3 | G–A | Val–Val |
| 5 | 188 | 3 | G–A | Ser–Ser |
| 5 | N.D. | N.D. | N.D. | N.D. |
| 9 | 336 | 1 | C–G | Leu–Val |
| 9 | 338 | 3 | C–T | Pro–Pro |

EXAMPLE 2

Production of Fusion OVCA1 Proteins

Fragments of the OVCA1 cDNA (Sequence I.D. No. 1) were ligated in the BamHI and EcoRI sites of the pGEX bacterial expression vector (commercially available). When expressed in bacteria, the pGEX vector produces a fusion protein between bacterial glutathione S-tranferase and the desired portions of the OVCA1 protein. E. coli cells were transformed with these constructs and the proteins prepared by inducing expression from an overnight culture with 0.1 mM IPTG for 2 hours. The cells were pelleted, washed with phosphate-buffered saline (PBS) and then sonicated. The bacterial debris was pelleted by centrifugation and the supernatant passed over a glutathione-Sepharose column. The protein was eluted using 5 mM glutathione in 50 mM Tris-HCl, pH 8.0. Protein yields have not yet been quantitated or optimized; however, this expression system routinely yields 1 mg of protein from 200 ml of bacterial cells.

The present invention is not limited to the embodiments described and exemplified above, but is capable of variation and modification without departure from the scope of the appended claims.

What is claimed is:

1. A vector, having ATCC Designation No. A97331, including a heterologous DNA segment from human chromosome 17p13.3, a contiguous sequence of at least 20 kilobase pairs of said segment being flanked by BssHII restriction sites and including locus D17S28 of said chromosome 17p13.3, said segment comprising at least one gene having 13 exons, the disruption of said at least one gene being associated with malignant cell growth.

2. An OVCA1 clone having ATCC designation No. 209189.

3. An OVCA2 clone having ATCC designation No. 209190.

* * * * *

UNITED STATES PATENT AND TRADEMARK OFFICE
CERTIFICATE OF CORRECTION

| | | |
|---|---|---|
| PATENT NO. | : 5,801,041 | |
| APPLICATION NO. | : 08/399986 | |
| DATED | : September 1, 1998 | |
| INVENTOR(S) | : Andrew K. Godwin | |

It is certified that error appears in the above-identified patent and that said Letters Patent is hereby corrected as shown below:

In the Specification

Column 1, Lines 4-7, delete the paragraph:
"Pursuant to 35 U.S.C. §202(c), it is hereby acknowledged that the U.S. Government has certain rights in the invention described herein, which was made in part with funds from the National Institutes of Health."

And insert therefor:
--This invention was made with government support under CA060643 awarded by the National Institutes of Health. The government has certain rights in the invention.--

Signed and Sealed this
Twenty-second Day of August, 2023

Katherine Kelly Vidal
*Director of the United States Patent and Trademark Office*

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
( A ) LENGTH: 2182 base pairs
( B ) TYPE: nucleic acid
( C ) STRANDEDNESS: double
( D ) TOPOLOGY: Not Relevant ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

```
ATGCGCAGGC AGGTGATGGC GGCGCTGGTC GTATCCGGGG CAGCGGAGCA GGGCGGCCGA    60

GACGGCCCTG GCAGAGGTCG GGCCCCTCGG GGCCGCGTGG CCAATCAGAT CCCCCCTGAG   120

ATCCTGAAGA ACCCTCAGCT GCAGGCAGCA ATCCGGGTCC TGCCTTCCAA CTACAACTTT   180

GAGATCCCCA AGACCATCTG GAGGATCCAA CAAGCCCAGG CCAAGAAGGT GGCCTTGCAA   240

ATGCCGGAAG GCCTCCTCCT CTTTGCCTGT ACCATTGTGG ATATCTTGGA AAGGTTCACG   300

GAGGCCGAAG TGATGGTGAT GGGTGACGTG ACCTACGGGG CTTGCTGTGT GGATGACTTC   360

ACAGCGAGGG CCCTGGGAGC TGACTTCTTG GTGCACTACG GCCACAGTTG CCTGATGCCC   420

ATGGACACCT CGGCCCAAGA CTTCCGGGTG CTGTACGTCT TTGTGGACAT CCGGATAGAC   480

ACTACACACC TCCTGGACTC TCTCCGCCTC ACCTTTCCCC CAGCCACTGC CCTTGCCCTG   540

GTCAGCACCA TTCAGTTTGT GTCGACCTTG CAGGCAGCCG CCCAGGAGCT GAAAGCCGAG   600

TATCGTGTGA GTGTCCACA GTGCAAGCCC CTGTCCCCTG GAGAGATCCT GGGCTGCACA   660

TCCCCCCGAC TGTCCAGAGA GGTGGAGGCC GTTGTGTATC TTGGAGATGG CCGCTTCCAT   720

CTGGAGTCTG TCATGATTGC CAACCCCAAT GTCCCCGCTT ACCGGTATGA CCCATATAGC   780

AAAGTCCTAT CCAGAGAACA CTATGACCAC CAGCGCATGC AGGCTGCTCG CCAAGAAGCC   840

ATAGCCACTG CCCGCTCAGC TAAGTCCTGG GGCCTTATTC TGGGCACTTT GGGCCGCCAG   900

GGCAGTCCTA AGATCCTGGA GCACCTGGAA TCTCGACTCC GAGCCTTGGG CCTTTCCTTT   960

GTGAGGCTGC TGCTCTCTGA GATCTTCCCC AGCAAGCTTA GCCTACTTCC CGAGGTGGAT  1020
```

-continued

| | | | | | |
|---|---|---|---|---|---|
| GTGTGGGTGC | AGGTGGCATG | TCCACGTCTC | TCCATTGACT | GGGGCACAGC | CTTCCCCAAG | 1080 |
| CCGCTGCTGA | CACCCTATGA | GGCGGCCGTG | GCTCTGAGGG | ACATTTCCTG | GCAGCAGCCC | 1140 |
| TACCCGATGG | ACTTCTACGC | TGGCAGCTCC | TTGGGGCCCT | GGACGGTGAA | CCACGGCCAG | 1200 |
| GACCGCCGTC | CCCACGCCCC | GGGCCGGCCC | GCGCGGGGGA | AGGTGCAGGA | GGGGTCCGCG | 1260 |
| CGTCCCCCTT | CGGCCGTGGC | TTGCGAGGAC | TGCAGCTGCA | GGGACGAGAA | GGTGGCGCCG | 1320 |
| CTGGCTCCTT | GACGCGCTCC | CGGGCCTCAG | GGTCCTGCCC | TCCGGAGGAG | CAGCCTCGAG | 1380 |
| GCTGGTGGTT | TTCAGAGCAG | GAGGCCGACG | TTTTCTCCGC | ATTGGAAGAG | CCCGCCGTCT | 1440 |
| GCAGGGGCCT | GGAGGAATCA | CTGGGGATGG | TGGCACAGGC | ACTGAACAGG | CTGGGGCCTT | 1500 |
| TTGACGGCCT | TCTTGGTTTC | AGCCAAGGGG | CTGCGCTAGC | AGCCCTTGTG | TGTGCCCTGG | 1560 |
| GCCAGGCAGG | CGATCCCCGC | TTCCCCTTGC | CACGGTTTAT | CCTCTTGGTG | TCTAGTTTCT | 1620 |
| GTCCCGGGG | CATTGGGTTC | AAGGAATCCA | TCCTCCAAAG | GCCCTTGTCA | TTGCCTTCGC | 1680 |
| TCCATGTTTT | TGGGGACACT | GACAAAGTCA | TCCCCTCTCA | GGAGAGTGTG | CAACTGGCCA | 1740 |
| GCCAATTTCC | CGGAGCCATC | ACCCTCACCC | ACTCTGGTGG | CCACTTCATT | CCAGCAGCTG | 1800 |
| CACCCCAGCG | TCAGGCCTAC | CTCAAGTTCT | GGACCAGTT | TGCAGAGTGA | AAGATCAAGA | 1860 |
| AATGTCTCTG | CTCCTACATC | CAGCTCCTCT | AGGGGCAGCC | TCCGTCATCC | ATGCCCTCCC | 1920 |
| AGGACCCTCC | ACTCACTGCT | GTGAGTGCGC | CTCACCAGAA | CCAGTTAAGA | GACAACTATC | 1980 |
| AATTCTTGAG | ACCCAAATTA | TAAGGGCCCT | GCCCTGTACT | GAAGAAAAGG | GGAGCACAAG | 2040 |
| GCCTTAATGG | ACATTGACTT | GTGAAAACGC | AAACATGAAT | ATGGTTGGAG | AGCCCTGGAT | 2100 |
| TAGGAGGGTG | ACATGGGGAA | GGCAGAGGCT | GGCACGATGG | TGACTGCCAC | ATAATAAAGT | 2160 |
| GGTGATTTGG | ATTTTGNAAA | AA | | | | 2182 |

( 2 ) INFORMATION FOR SEQ ID NO:2:

( i ) SEQUENCE CHARACTERISTICS:
      ( A ) LENGTH: 443 amino acids
      ( B ) TYPE: amino acid
      ( C ) STRANDEDNESS: Not Relevant
      ( D ) TOPOLOGY: Not Relevant ( i i ) MOLECULE TYPE: protein ( i i i ) HYPOTHETICAL: NO ( i v ) ANTI-SENSE: NO ( x i ) SEQUENCE DESCRIPTION: SEQ ID NO:2:

```
Met Arg Arg Gln Val Met Ala Ala Leu Val Val Ser Gly Ala Ala Glu
 1               5                  10                  15

Gln Gly Gly Arg Asp Gly Pro Gly Arg Gly Arg Ala Pro Arg Gly Arg
            20                  25                  30

Val Ala Asn Gln Ile Pro Pro Glu Ile Leu Lys Asn Pro Gln Leu Gln
        35                  40                  45

Ala Ala Ile Arg Val Leu Pro Ser Asn Tyr Asn Phe Glu Ile Pro Lys
    50                  55                  60

Thr Ile Trp Arg Ile Gln Gln Ala Gln Ala Lys Lys Val Ala Leu Gln
65                  70                  75                  80

Met Pro Glu Gly Leu Leu Leu Phe Ala Cys Thr Ile Val Asp Ile Leu
                85                  90                  95

Glu Arg Phe Thr Glu Ala Glu Val Met Val Met Gly Asp Val Thr Tyr
            100                 105                 110

Gly Ala Cys Cys Val Asp Asp Phe Thr Ala Arg Ala Leu Gly Ala Asp
```

|     |     |     |     |     | 115 |     |     |     |     | 120 |     |     |     |     | 125 |     |
|-----|-----|-----|-----|-----|-----|-----|-----|-----|-----|-----|-----|-----|-----|-----|-----|-----|

Phe Leu Val His Tyr Gly His Ser Cys Leu Met Pro Met Asp Thr Ser
130                     135                 140

Ala Gln Asp Phe Arg Val Leu Tyr Val Phe Val Asp Ile Arg Ile Asp
145                 150                 155                 160

Thr Thr His Leu Leu Asp Ser Leu Arg Leu Thr Phe Pro Pro Ala Thr
                165                 170                 175

Ala Leu Ala Leu Val Ser Thr Ile Gln Phe Val Ser Thr Leu Gln Ala
            180                 185                 190

Ala Ala Gln Glu Leu Lys Ala Glu Tyr Arg Val Ser Val Pro Gln Cys
        195                 200                 205

Lys Pro Leu Ser Pro Gly Glu Ile Leu Gly Cys Thr Ser Pro Arg Leu
210                 215                 220

Ser Arg Glu Val Glu Ala Val Val Tyr Leu Gly Asp Gly Arg Phe His
225                 230                 235                 240

Leu Glu Ser Val Met Ile Ala Asn Pro Asn Val Pro Ala Tyr Arg Tyr
                245                 250                 255

Asp Pro Tyr Ser Lys Val Leu Ser Arg Glu His Tyr Asp His Gln Arg
            260                 265                 270

Met Gln Ala Ala Arg Gln Glu Ala Ile Ala Thr Ala Arg Ser Ala Lys
        275                 280                 285

Ser Trp Gly Leu Ile Leu Gly Thr Leu Gly Arg Gln Gly Ser Pro Lys
    290                 295                 300

Ile Leu Glu His Leu Glu Ser Arg Leu Arg Ala Leu Gly Leu Ser Phe
305                 310                 315                 320

Val Arg Leu Leu Leu Ser Glu Ile Phe Pro Ser Lys Leu Ser Leu Leu
                325                 330                 335

Pro Glu Val Asp Val Trp Val Gln Val Ala Cys Pro Arg Leu Ser Ile
            340                 345                 350

Asp Trp Gly Thr Ala Phe Pro Lys Pro Leu Leu Thr Pro Tyr Glu Ala
        355                 360                 365

Ala Val Ala Leu Arg Asp Ile Ser Trp Gln Gln Pro Tyr Pro Met Asp
370                 375                 380

Phe Tyr Ala Gly Ser Ser Leu Gly Pro Trp Thr Val Asn His Gly Gln
385                 390                 395                 400

Asp Arg Arg Pro His Ala Pro Gly Arg Pro Ala Arg Gly Lys Val Gln
                405                 410                 415

Glu Gly Ser Ala Arg Pro Pro Ser Ala Val Ala Cys Glu Asp Cys Ser
            420                 425                 430

Cys Arg Asp Glu Lys Val Ala Pro Leu Ala Pro
        435                 440

( 2 ) INFORMATION FOR SEQ ID NO:3:

( i ) SEQUENCE CHARACTERISTICS:
  ( A ) LENGTH: 1016 base pairs
  ( B ) TYPE: nucleic acid
  ( C ) STRANDEDNESS: double
  ( D ) TOPOLOGY: Not Relevant ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

ATGGCCGCGC AGCGACCCCT GCGGGTCCTG TGCCTGGCGG GCTTCCGGCA GAGCGAGCGG  60

```
GGCTTCCGTG AGAAGACCGG GGCGCTGAGG AAGGCGCTGC GGGGTCGCGC CGAGCTCGTG      120

TGCCTCAGCG GCCCGCACCC GGTCCCCGAC CCCCGGGCC CCGAGGGCGC CAGATCAGAC       180

TTCGGGTCCT GCCCTCCGGA GGAGCAGCCT CGAGGCTGGT GGTTTTCAGA GCAGGAGGCC      240

GACGTTTTCT CCGCATTGGA AGAGCCCGCC GTCTGCAGGG GCCTGGAGGA ATCACTGGGG      300

ATGGTGGCAC AGGCACTGAA CAGGCTGGGG CCTTTTGACG GCCTTCTTGG TTTCAGCCAA      360

GGGGCTGCGC TAGCAGCCCT TGTGTGTGCC CTGGGCCAGG CAGGCGATCC CCGCTTCCCC      420

TTGCCACGGT TTATCCTCTT GGTGTCTAGT TTCTGTCCCC GGGCATTGG GTTCAAGGAA       480

TCCATCCTCC AAAGGCCCTT GTCATTGCCT TCGCTCCATG TTTTGGGGA CACTGACAAA       540

GTCATCCCCT CTCAGGAGAG TGTGCAACTG GCCAGCCAAT TCCCGGAGC CATCACCCTC       600

ACCCACTCTG GTGGCCACTT CATTCCAGCA GCTGCACCCC AGCGTCAGGC CTACCTCAAG      660

TTCTTGGACC AGTTTGCAGA GTGAAAGATC AAGAAATGTC TCTGCTCCTA CATCCAGCTC      720

CTCTAGGGGC AGCCTCCGTC ATCCATGCCC TCCCAGGACC CTCCACTCAC TGCTGTGAGT      780

GCGCCTCACC AGAACCAGTT AAGAGACAAC TATCAATTCT TGAGACCCAA ATTATAAGGG      840

CCCTGCCCTG TACTGAAGAA AAGGGGAGCA CAAGGCCTTA ATGGACATTG ACTTGTGAAA      900

ACGCAAACAT GAATATGGTT GGAGAGCCCT GGATTAGGAG GGTGACATGG GGAAGGCAGA      960

GGCTGGCACG ATGGTGACTG CCACATAATA AAGTGGTGAT TTGGATTTTG NAAAAA         1016
```

( 2 ) INFORMATION FOR SEQ ID NO:4:

( i ) SEQUENCE CHARACTERISTICS:
        ( A ) LENGTH: 526 amino acids
        ( B ) TYPE: amino acid
        ( C ) STRANDEDNESS: Not Relevant
        ( D ) TOPOLOGY: Not Relevant ( i i ) MOLECULE TYPE: protein ( i i i ) HYPOTHETICAL: NO ( i v ) ANTI-SENSE: NO ( v i i i ) POSITION IN GENOME:
        ( A ) CHROMOSOME/SEGMENT: IX Cosmid 9150

( x i ) SEQUENCE DESCRIPTION: SEQ ID NO:4:

```
Met  Ser  Gly  Ser  Thr  Glu  Ser  Lys  Lys  Gln  Pro  Arg  Arg  Arg  Phe  Ile
 1              5                        10                       15

Gly  Arg  Lys  Ser  Gly  Asn  Ser  Asn  Asn  Asp  Lys  Leu  Thr  Thr  Val  Ala
              20                       25                       30

Glu  Asn  Gly  Asn  Glu  Ile  Ile  His  Lys  Gln  Lys  Ser  Arg  Ile  Ala  Leu
              35                       40                       45

Gly  Arg  Ser  Val  Asn  His  Val  Pro  Glu  Asp  Ile  Leu  Asn  Asp  Lys  Glu
         50                       55                       60

Leu  Asn  Glu  Ala  Ile  Lys  Leu  Leu  Pro  Ser  Asn  Tyr  Asn  Phe  Glu  Ile
 65                       70                       75                       80

His  Lys  Thr  Val  Trp  Asn  Ile  Arg  Lys  Tyr  Asn  Ala  Lys  Arg  Ile  Ala
                   85                       90                       95

Leu  Gln  Met  Pro  Glu  Gly  Leu  Leu  Ile  Tyr  Ser  Leu  Ile  Ile  Ser  Asp
                  100                      105                     110

Ile  Leu  Glu  Gln  Phe  Cys  Gly  Val  Glu  Thr  Leu  Val  Met  Gly  Asp  Val
              115                      120                      125

Ser  Tyr  Gly  Ala  Cys  Cys  Ile  Asp  Asp  Phe  Thr  Ala  Arg  Ala  Leu  Asp
         130                      135                      140
```

```
Cys Asp Phe Ile Val His Tyr Ala His Ser Cys Leu Val Pro Ile Asp
145                 150                 155                 160

Val Thr Lys Ile Lys Val Leu Tyr Val Phe Val Thr Ile Asn Ile Gln
                165                 170                 175

Glu Asp His Ile Ile Lys Thr Leu Gln Lys Asn Phe Pro Lys Gly Ser
            180                 185                 190

Arg Ile Ala Thr Phe Gly Thr Ile Gln Phe Asn Pro Ala Val His Ser
        195                 200                 205

Val Arg Asp Lys Leu Leu Asn Asp Glu His Met Leu Tyr Ile Ile
210                 215                 220

Pro Pro Gln Ile Lys Pro Leu Ser Arg Gly Glu Val Leu Gly Cys Thr
225                 230                 235                 240

Ser Glu Arg Leu Asp Lys Glu Gln Tyr Asp Ala Met Val Phe Ile Gly
                245                 250                 255

Asp Gly Arg Phe His Leu Glu Ser Ala Met Ile His Asn Pro Glu Ile
            260                 265                 270

Pro Ala Phe Lys Tyr Asp Pro Tyr Asn Arg Lys Phe Thr Arg Glu Gly
        275                 280                 285

Tyr Asp Gln Lys Gln Leu Val Glu Val Arg Ala Glu Ala Ile Glu Val
    290                 295                 300

Ala Arg Lys Gly Lys Val Phe Gly Leu Ile Leu Gly Ala Leu Gly Arg
305                 310                 315                 320

Gln Gly Asn Leu Asn Thr Val Lys Asn Leu Glu Lys Asn Leu Ile Ala
                325                 330                 335

Ala Gly Lys Thr Val Val Lys Ile Ile Leu Ser Glu Val Phe Pro Gln
            340                 345                 350

Lys Leu Ala Met Phe Asp Gln Ile Asp Val Phe Val Gln Val Ala Cys
        355                 360                 365

Pro Arg Leu Ser Ile Asp Trp Tyr Ala Phe Asn Lys Pro Leu Leu Thr
370                 375                 380

Pro Tyr Glu Ala Ser Val Leu Leu Lys Lys Asp Val Met Phe Ser Glu
385                 390                 395                 400

Lys Tyr Tyr Pro Met Asp Tyr Tyr Glu Ala Ala Lys Gly Tyr Gly Arg
                405                 410                 415

Gly Glu Thr Pro Lys Glu Ala Ile Glu Met Leu Lys Val Glu Lys Phe
            420                 425                 430

Lys Lys Leu Lys Arg Phe Glu Val Tyr Tyr Cys Leu Lys Asn Ser Phe
        435                 440                 445

Leu Glu Glu Val Asp Ile Glu Met Lys Tyr Ser Cys Ser Ile Thr Thr
    450                 455                 460

Ile Lys Ser Asn Gly Ser Ala Ser Leu Leu Met Asn Trp Glu Glu Leu
465                 470                 475                 480

Thr Pro Gly His Cys Phe Thr Ser Tyr Thr Thr Asn Pro Ile Ala Gly
                485                 490                 495

Asp Tyr Gly Leu Asn Ala Ser Ala Ile Asp Gly His Thr Glu Glu Leu
            500                 505                 510

Val Ala Thr His Pro Ala Gly Thr Leu Glu Asn Ala Thr Gln
        515                 520                 525
```

( 2 ) INFORMATION FOR SEQ ID NO:5:

( i ) SEQUENCE CHARACTERISTICS:
        ( A ) LENGTH: 661 amino acids
        ( B ) TYPE: amino acid
        ( C ) STRANDEDNESS: Not Relevant
        ( D ) TOPOLOGY: Not Relevant ( i i ) MOLECULE TYPE: protein ( i i i ) HYPOTHETICAL: NO ( i v ) ANTI-SENSE: NO ( x i ) SEQUENCE DESCRIPTION: SEQ ID NO:5:

```
Met  Ile  Thr  Phe  Gln  Leu  Pro  Ser  Asn  Tyr  Thr  Phe  Glu  Val  Pro  Lys
1                    5                   10                            15

Thr  Ile  Trp  Lys  Ile  Arg  Ser  Thr  Glu  Ser  Lys  Tyr  Val  Ala  Leu  Gln
               20                   25                       30

Phe  Pro  Glu  Gly  Leu  Ile  Met  Tyr  Ala  Cys  Val  Ile  Ala  Asp  Ile  Leu
          35                        40                        45

Glu  Lys  Tyr  Thr  Gly  Cys  Asp  Thr  Val  Ile  Met  Gly  Asp  Val  Thr  Tyr
     50                   55                        60

Gly  Ala  Cys  Cys  Val  Asp  Asp  Thr  Tyr  Ala  Lys  Ser  Met  Gly  Cys  Asp
65                  70                        75                            80

Leu  Leu  Val  His  Tyr  Gly  His  Ser  Cys  Leu  Val  Pro  Ile  Gln  Asn  Thr
               85                        90                            95

Asp  Gly  Ile  Ala  Met  Leu  Tyr  Val  Phe  Gly  Lys  Arg  Leu  Val  Val  Val
               100                       105                 110

Ser  Thr  Val  Gln  Phe  Ile  Pro  Ser  Leu  Gln  Thr  Leu  Arg  Thr  Thr  Phe
          115                      120                      125

Asn  Lys  Asp  Asp  Ser  Ser  Ile  Arg  Ile  Asp  Ile  Pro  Gln  Cys  Lys  Pro
     130                      135                      140

Leu  Ser  Pro  Gly  Glu  Val  Leu  Gly  Cys  Thr  Ser  Pro  Arg  Leu  Asp  Ala
145                      150                      155                      160

Ser  Lys  Tyr  Asp  Ala  Ile  Val  Tyr  Leu  Gly  Asp  Gly  Arg  Phe  His  Leu
               165                       170                      175

Glu  Ser  Ile  Met  Ile  His  Asn  Pro  Glu  Ile  Glu  Ala  Phe  Gln  Tyr  Asp
               180                       185                      190

Pro  Tyr  Ser  Arg  Lys  Leu  Thr  Arg  Glu  Phe  Tyr  Asp  His  Asp  Leu  Met
          195                      200                      205

Arg  Lys  Asn  Arg  Ile  Gly  Ser  Ile  Glu  Ile  Ala  Arg  Lys  Cys  Thr  Thr
     210                      215                      220

Phe  Gly  Leu  Ile  Gln  Gly  Thr  Leu  Gly  Arg  Gln  Gly  Asn  Leu  Lys  Val
225                      230                      235                      240

Val  Glu  Glu  Leu  Glu  Ala  Gln  Leu  Glu  Arg  Lys  Gly  Lys  Lys  Phe  Leu
               245                      250                      255

Arg  Val  Leu  Leu  Ser  Glu  Ile  Phe  Pro  Glu  Lys  Leu  Ala  Met  Phe  Pro
               260                      265                      270

Glu  Val  Asp  Cys  Trp  Val  Gln  Val  Ala  Cys  Pro  Arg  Leu  Ser  Ile  Asp
          275                      280                      285

Trp  Gly  Thr  Gln  Phe  Pro  Lys  Pro  Leu  Leu  Tyr  Pro  Phe  Glu  Leu  Ala
     290                      295                      300

Val  Ala  Leu  Asp  Asn  Val  Ser  Phe  Lys  Phe  Arg  Cys  Leu  Gln  Ile  Thr
305                      310                      315                      320

Gly  Gln  Trp  Thr  Ile  Ile  Arg  Met  Ile  Pro  Trp  Val  Leu  Gly  Arg  Ile
               325                      330                      335

Ile  Met  Lys  Arg  Thr  Val  Arg  Asn  Gly  Arg  Asn  Gly  Asn  Leu  Ile  Leu
               340                      345                      350

Leu  Ser  Lys  Pro  Lys  Ile  His  Ser  Arg  Glu  Leu  Ser  Tyr  Phe  Asn  Glu
          355                      360                      365

Glu  Lys  Ala  Lys  Arg  Ile  Gly  Glu  Arg  Phe  Glu  Gly  Gly  Lys  Leu  Ala
     370                      375                      380
```

| Lys 385 | Lys | Val | His | Lys | Ser 390 | Ile | Glu | Gln | Leu | Lys 395 | Arg | His | Asp | Pro 400 |
| Trp | Gln | Ile | Ser | Thr 405 | Glu | Pro | Thr | Lys | Tyr 410 | Leu | Leu | Val | Ser | Asn 415 | Ser |
| Ser | Ile | Leu | Cys 420 | Gly | Val | Ser | Leu | Glu 425 | Leu | Glu | Glu | Ile 430 | Phe | Leu |
| Pro | Leu | Asp 435 | Glu | Leu | Ala | Glu | Phe 440 | Ile | Val | Tyr | Pro | Asn 445 | Lys | Arg | Ser |
| Tyr | Ser 450 | Phe | Val | Gln | Cys | Ser 455 | Ser | Ile | Glu | Lys | Ser 460 | Ile | Gln | Val | Arg |
| Thr 465 | Glu | Leu | His | Gly | Leu 470 | Ile | Pro | Pro | Ser | Leu 475 | Lys | Asn | Ser | His | Gln 480 |
| Pro | Phe | Ala | Ile | Ser 485 | Tyr | Val | Glu | Asn | Leu 490 | Pro | Glu | Ala | Thr | Lys 495 | Cys |
| Glu | Asp | Phe | Arg 500 | Pro | Ala | Asn | Leu | Lys 505 | Ile | Ile | Glu | Glu | Tyr 510 | Val | Ser |
| Ser | Asp | Leu 515 | Glu | Lys | Glu | Leu | Val 520 | Asp | Leu | Val | Thr | Asn 525 | His | Pro | Ser |
| Val | Gln 530 | Ser | Leu | Lys | His | Arg 535 | Ala | Val | Val | His | Phe 540 | Gly | His | Val | Phe |
| Asp 545 | Tyr | Ser | Thr | Asn | Ser 550 | Ala | Ser | Glu | Trp | Lys 555 | Glu | Ala | Asp | Pro | Ile 560 |
| Pro | Pro | Val | Ile | Asn 565 | Ser | Leu | Ile | Asp | Arg 570 | Leu | Ile | Ser | Asp | Lys 575 | Tyr |
| Ile | Thr | Glu | Arg 580 | Pro | Asp | Gln | Val | Thr 585 | Ala | Asn | Val | Tyr | Glu 590 | Ser | Gly |
| His | Gly | Ile 595 | Pro | Ser | His | Tyr | Asp 600 | Thr | His | Ser | Ala | Phe 605 | Asp | Asp | Pro |
| Ile | Val 610 | Ser | Ile | Ser | Leu | Leu 615 | Asp | Lys | Val | Val | Met 620 | Glu | Phe | Lys | Asp |
| Gly 625 | Glu | Asn | Ser | Ala | Arg 630 | Ile | Ala | Pro | Val | Leu 635 | Leu | Lys | Ala | Arg | Ser 640 |
| Leu | Cys | Leu | Ile | Gln 645 | Gly | Glu | Ser | Arg | Tyr 650 | Arg | Trp | Lys | His | Gly 655 | Ile |
| Val | Asn | Arg | Lys 660 | Tyr |

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:6:

CGCCCTATC TCCTCCTTTA     20

(2) INFORMATION FOR SEQ ID NO:7:

(i) SEQUENCE CHARACTERISTICS:
        (A) LENGTH: 20 base pairs
        (B) TYPE: nucleic acid -continued ( C ) STRANDEDNESS: single
                ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:7:

TGGTCCTGTC CCTAACTTGG                                                    20

( 2 ) INFORMATION FOR SEQ ID NO:8:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:8:

CATCTCAATC TGGCTTCAGC                                                    20

( 2 ) INFORMATION FOR SEQ ID NO:9:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:9:

AACCCCAGCT CAATGATCAC                                                    20

( 2 ) INFORMATION FOR SEQ ID NO:10:

( i ) SEQUENCE CHARACTERISTICS:
                ( A ) LENGTH: 19 base pairs
                ( B ) TYPE: nucleic acid
                ( C ) STRANDEDNESS: single
                ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:10:

CTAGCCCTCC ACCTCTCAT                                                     19

( 2 ) INFORMATION FOR SEQ ID NO:11:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:11:

AGCCTGGCTC ACCCTCCT   18

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:12:

AGGGTGGGTC TCTCCTAC   18

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:13:

ATGGGGAAGA TGAATGTG   18

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:14:

CCTCTGCTGC TCCTACCT   18

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:15:

TGTCCACCCT ACAGGAGG                                                                                           18

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:16:

CTCTCCTGCC CCAGCCGTTG G                                                                                       21

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:17:

GATGAACCTA AGACTCCCTC C                                                                                       21

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:18:

CTTCTGCTGC CCTAAACCAC                                                                                         20

( 2 ) INFORMATION FOR SEQ ID NO:19:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:19:

AGTGGCAGGG AATCTCACC                                                                                          19

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:20:

CTGAGTCAGG ATCTGTGTGC A        21

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:21:

TGTTCCCAGT CACTTCCCTC        20

( 2 ) INFORMATION FOR SEQ ID NO:22:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:22:

TAGGCCAGCG GTTCAGCTTT        20

( 2 ) INFORMATION FOR SEQ ID NO:23:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:23:

CAGCCTTCAA GACGAGCTG        19

( 2 ) INFORMATION FOR SEQ ID NO:24:

(  i  ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:24:

CACTGTCACG TTCTTCAGCA      20

( 2 ) INFORMATION FOR SEQ ID NO:25:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:25:

ACCCCACTCC ACTCCAGAC      19

( 2 ) INFORMATION FOR SEQ ID NO:26:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:26:

ACACTGGCAG ATGTTATTGT CC      22

( 2 ) INFORMATION FOR SEQ ID NO:27:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:27:

CTCCTCCCTC CTGGAAGC      18

( 2 ) INFORMATION FOR SEQ ID NO:28:

( i ) SEQUENCE CHARACTERISTICS:
    ( A ) LENGTH: 18 base pairs
    ( B ) TYPE: nucleic acid
    ( C ) STRANDEDNESS: single ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:28:

GGAGGGAAAC GCAGGGTC                                                                 18

( 2 ) INFORMATION FOR SEQ ID NO:29:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:29:

AGGCGTTCCC ATGACAAC                                                                 18

( 2 ) INFORMATION FOR SEQ ID NO:30:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:30:

GAGGCTGGTG GTTTTCAGAG C                                                             21

( 2 ) INFORMATION FOR SEQ ID NO:31:

( i ) SEQUENCE CHARACTERISTICS:
                ( A ) LENGTH: 22 base pairs
                ( B ) TYPE: nucleic acid
                ( C ) STRANDEDNESS: single
                ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:31:

GGGACAGAAA CGAGACACCA AG                                                            22

( 2 ) INFORMATION FOR SEQ ID NO:32:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: Not Relevant ( i i ) MOLECULE TYPE: DNA (genomic)

(iii) HYPOTHETICAL: NO (iv) ANTI-SENSE: YES (xi) SEQUENCE DESCRIPTION: SEQ ID NO:32:

GGGTTTATCC TCTTGGTGTC T                                                         21

(2) INFORMATION FOR SEQ ID NO:33:

(i) SEQUENCE CHARACTERISTICS:
        (A) LENGTH: 21 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:33:

CATTTCTTGA TCTTTCACTC T                                                         21

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:34:

TGGACCAGTT TGCAGAGTGA                                                           20

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:35:

TATCTGGCAG TCACCATCGT                                                           20